United States Patent
Chiba et al.

(10) Patent No.: US 7,579,166 B2
(45) Date of Patent: Aug. 25, 2009

(54) GLYCOPROTEIN AND PROCESS FOR PRODUCING THE SAME

(75) Inventors: Yasunori Chiba, Ibaraki (JP); Yoshifumi Jigami, Ibaraki (JP); Hitoshi Sakuraba, Tokyo (JP); Kazuo Kobayashi, Gumma (JP); Makoto Takeuchi, Kanagawa (JP); Yoriko Takeuchi, legal representative, Kanagawa (JP)

(73) Assignees: National Institute of Advanced Industrial Science and Technology, Tokyo (JP); Tokyo Metropolitan Organization for Medical Research, Tokyo (JP)

(*) Notice: Subject to any disclaimer, the term of this patent is extended or adjusted under 35 U.S.C. 154(b) by 793 days.

(21) Appl. No.: 10/480,790

(22) PCT Filed: Jun. 14, 2002

(86) PCT No.: PCT/JP02/05965

§ 371 (c)(1),
(2), (4) Date: Jun. 24, 2004

(87) PCT Pub. No.: WO02/103027

PCT Pub. Date: Dec. 27, 2002

(65) Prior Publication Data

US 2005/0064539 A1    Mar. 24, 2005

(30) Foreign Application Priority Data

Jun. 14, 2001    (JP) .............................. 2001-180907

(51) Int. Cl.
*C12N 15/00* (2006.01)
*C12P 21/00* (2006.01)
*C12Q 1/68* (2006.01)
*C07K 14/00* (2006.01)

(52) U.S. Cl. ........................ 435/69.1; 435/6; 435/71.1

(58) Field of Classification Search ........................ None
See application file for complete search history.

(56) References Cited

U.S. PATENT DOCUMENTS 5,401,650 A * 3/1995 Desnick et al. ............. 435/208

5,854,031 A    12/1998 Nakayama et al.

FOREIGN PATENT DOCUMENTS

EP          1 211 310 A       6/2002
WO      WO 01/19955 A       3/2001

OTHER PUBLICATIONS

Supplementary European Search Report of EP 02 73 6110.
K. Takegawa et al., "Purification and Properties of a Low-Molecular-Weight Alpha Mannosidase From *Cellulomonas*-sp", Journal of Fermentation and Bioengineering, vol. 69, No. 2, 1990, pp. 129-131.
Yasunori Chiba et al., "Production in yeast of α-galactosidase-A, a lysosomal enzyme applicable to enzyme replacement therapy for Fabry disease", Glycobiology, vol. 12, No. 12, pp. 821-828, 2002.
JP 3091851 B2 (Director General, Agency of Industrial Science and Tehcnology) Jul. 28, 2000.
JP 10-155495 A (Director General, Agency of Industrial Science and Technology) Jun. 16, 1998.
R. Schiffman, et al., Infusion of α-galactosidase A reduces tissue globotriaosylceramide storage in patients with Fabry disease. Proc. Natl. Acad. Sci. USA, Jan. 2000, vol. 97, No. 1, pp. 365-370.

* cited by examiner

*Primary Examiner*—Nancy Vogel
*Assistant Examiner*—Michele K. Joike
(74) *Attorney, Agent, or Firm*—Stephen A. Bent; Foley & Lardner LLP

(57) ABSTRACT

A process for producing a lysosomal enzyme having a mannose-6-phosphate-containing acidic sugar chain, wherein the process comprising: culturing in a medium yeast cells obtained by introducing a lysosomal enzyme gene into a sugar chain biosynthetic enzyme gene mutant strain of yeast, collecting a lysosomal enzyme having a phosphate-containing sugar chain from the culture, and then treating the enzyme with α-mannosidase; and pharmaceutical compositions for treatment of human lysosomal enzyme deficiencies produced by the process. The genetic engineering technique using the yeast according to the present invention allows large-amount and high-purity production of a glycoprotein having a phosphate-containing acidic sugar chain which can serve as a labeling marker for transporting into lysosomes in cells of mammals such as human. The glycoprotein having a phosphate-containing acidic sugar chain according to the invention may be utilized as a drug effective in treatment of human lysosomal enzyme deficiencies, etc.

11 Claims, 11 Drawing Sheets
(3 of 11 Drawing Sheet(s) Filed in Color)

\*: Potential phosphorylation site
n : 50-100
m : 10-25

GLYCOPROTEIN AND PROCESS FOR PRODUCING THE SAME

TECHNICAL FIELD

The present invention relates to a process for production of glycoproteins having mannose-6-phosphate-containing acidic sugar chains in which the sugar chains can serve as labeling markers for transporting the glycoproteins to lysosomes in cells of mammal such as human.

BACKGROUND ART

It has become evident that naturally occurring proteins fail to exhibit their inherent biological activity when their sugar chains are removed (A. Kibata, Tanpakushitsu Kakusan Koso 36, 775-788 (1991)). This suggests that sugar chains play an important role in developing biological activity. However, because the correlation between sugar chain structure and biological activity is not always apparent, the development of techniques allowing flexible modification and control of the structures (the types of sugars, the linked positions, chain lengths, etc.) of sugar chains attached to proteins is needed.

Glycoprotein sugar chains are largely classified as Asn-linked types, mucin types, O-GlcNAc types, GPI anchored types and proteoglycan types (M. Takeuchi, Glycobiology Series 5, Glycotechnology; edited by A. Kibata, S. Hakomori, K. Nagai, Kodansha Scientific, 191-208 (1994)), each of which have unique routes of biosynthesis and carry out different physiological functions. The biosynthesis pathway for Asn-linked sugar chains has been widely studied and analyzed in detail.

Biosynthesis of Asn-linked sugar chains begins with synthesis of a precursor consisting of N-acetylglucosamine, mannose and glucose on a lipid carrier intermediate, and its transfer to a specific sequence (Asn-X-Ser or Thr) of the glycoprotein in the endoplasmic reticulum (ER). It then undergoes processing (cleavage of the glucose residue and a specific mannose residue) to synthesize an M8 high mannose-type sugar chain composed of 8 mannose residues and 2 N-acetylglucosamine residues (Man8GlcNAc2). The protein including the high mannose-type sugar chain is transported to the Golgi apparatus where it undergoes various modifications, and these modifications at the Golgi apparatus differ significantly between yeast and mammals (Kukuruzinska et al., Ann. Rev. Biochem., 56, 915-944 (1987)).

In mammalian cells, one of three different pathways are taken, depending on the type of protein undergoing the sugar chain modification. The three pathways are cases 1) where the core sugar chain is not altered, 2) where the N-acetylglucosamine-1-phosphate moiety (GlcNAc-1-P) of UDP-N-acetylglucosamine (UDP-GlcNAc) is added at the 6-position of Man of the core sugar chain producing Man-6-P-1-GlcNAc, after which only the GlcNAc moiety is removed, for conversion to a glycoprotein having an acidic sugar chain, and 3) where five molecules of Man are removed in order from the core sugar chain, leaving Man3GlcNAc2 onto which almost simultaneously GlcNAc, galactose (Gal) and N-acetylneuraminic acid (also known as sialic acid (NeuNAc)) are added in order, resulting in a mixture of diverse hybrid and complex sugar chains [R. Kornfeld and S. Kornfeld, Ann. Rev. Biochem., Vol. 54, p.631-664 (1985)] (FIG. 1). Thus, it has been found that mammalian sugar chains have a variety of structures which are closely related to the functions of glycoproteins.

On the other hand, it has been found that yeast produce mannan-type sugar chains, or "outer chains", having several to a hundred mannose residues on the above-mentioned core sugar chain (Man8GlcNAc2), while acidic sugar chains are also produced having mannose-1-phosphate added to the core sugar chain moiety and outer chain moiety (see FIG. 2). This modification differs from that of animal cells, and it has been reported that in yeast it does not function as a sorting signal for localization of glycoproteins to vacuoles (organelles corresponding to lysosomes in animal cells). The physiological function of phosphorylated sugar chains in yeast has therefore remained a mystery [Kukuruzinska et al, Ann. Rev. Biochem., Vol.56, p915-944 (1987)].

As shown in FIG. 2, the phosphorylation sites of mannose phosphate-containing sugar chains in yeast are sometimes added to the α-1,3 branch side and α-1,6 branch side of the Man8GlcNAc2 core sugar chain synthesized in the ER, and are sometimes added to the α-1,2 branches abundantly present on mannose outer chains synthesized in the Golgi apparatus, or to the non-reducing ends of mannose outer chains [Herscovics and P. Orlean, FASEB J., Vol. 7, p540-550 (1993)].

Biosynthesis of outer chains in *Saccharomyces* yeast is believed to occur along the pathway shown in FIG. 2 [Ballou et al., Proc. Natl. Acad. Sci. USA, Vol.87, p3368 (1990)].

Specifically, an elongation initiating reaction occurs wherein mannose is added to the M8 high mannose-type sugar chains at the α-1,6 linkages (FIG. 2, Reactions I, B). It has been shown that the enzyme responsible for this reaction is a protein encoded by the OCH1 gene (Nakayama et al., EMBO J., 11, 2511-2519 (1992)). Also, a reaction of successive elongation of mannose by α-1,6 linkages (FIG. 2: II) forms poly α-1,6-linked mannose as the skeletons of the outer chains (FIG. 2: E). The α-1,6-linked mannose has α-1,2-linked mannose branches (FIG. 2: C, F, H), and α-1,3-linked mannose is often added to the ends of the branching α-1,2-linked mannose (FIG. 2: D, G, H, I). The addition of these α-1,3-linked mannoses is performed by MNN1 gene product (Nakanishi-Shindo et al., J. Biol. Chem., 268, 26338-26345 (1993)). It has also become evident that some acidic sugar chains are produced having mannose-1-phosphate added to the high mannose-type sugar chain moieties (FIG. 2: *) and outer chain moieties. This reaction has been shown to depend on a protein encoded by the MNN6 gene (Wang et al., J. Biol. Chem., 272, 18117-18124 (1997)), while a gene (MNN4) has also been identified which codes for a protein which positively controls this transfer reaction (Odani et al., Glycobiology, 6, 805-810 (1996); Odani et al., FEBS letters, 420, 186-190 (1997)).

In most cases, outer chains result in heterogeneous protein products, both complicating protein purification and lowering specific activity (Bekkers et al., Biochim. Biophys. Acta, 1089, 345-351 (1991)). Moreover, because of the vast differences in sugar chain structures, glycoproteins produced in yeast do not exhibit the same biological activity as those from mammals, and are strongly immunogenic in mammals. For example, it is known that the α-1,3 mannoside linkages produced by the MNN1 gene in *S. cerevisiae* have strong immunogenicity (Ballou, C. E., Methods Enzymol., 185, 440-470 (1990)). It has been also reported that yeast inherently possess mannose-6-phosphate (Man-6-P) in the form of mannose-6-phosphate-α-1-mannose (Man-6-P-1-Man), which do not bind to Man-6-P receptors (Kukuruzinska et al., Annu. Rev. Biochem., 56, 915-944 (1987); Faust and Kornfeld, J. Biol. Chem., 264, 479-488 (1989); Tong et al., J. Biol. Chem., 264, 7962-7969 (1989)). Thus, yeast are considered unsuitable as hosts for production of useful mammalian glycoproteins. It has been a desire in both academia and industry to develop yeast that can produce glycoproteins with sugar chains having mammalian-equivalent biological activity, i.e., mammalian-type sugar chains. The present inventors have previously succeeded in creating mutants lacking outer chains and yeast with mammalian-type sugar chains (Japanese Patent Application No. 11-233215).

As mentioned above, yeast produce acidic sugar chains having mannose-1-phosphate added to the core sugar chain moiety and outer chain moiety by the action of the MNN4 gene and MNN6 gene. It has been demonstrated that sugar chains of glycoproteins produced by mutants which produce the core sugar chain and are deficient in the genes for the outer chain synthetic enzymes, include both neutral sugar chains (FIG. 3: Structural Formula I) and acidic sugar chains (FIG. 3: Structural Formulas II to IV) (Proceedings of the 12th Biotechnology Symposium, p.153-157, Oct. 14, 2004, Biotechnology Developmental Technology Research Society).

Such acidic sugar chains have a structure not found in mammalian sugar chains. Specifically, in mammalian cells it is not mannose-1-phosphate but rather N-acetylglucosamine-1-phosphate which is added, after which the N-acetylglucosamine moiety alone is removed to produce the final acidic sugar chain marked as "*" in FIG. 1. As will be further explained below and is taught in Methods in Enzymology, [Vol.185, p.440-470 (1990)], this sugar chain serves as a lysosome transport signal in mammalian cells.

Lysosomes are intracellular organelles containing numerous acidic hydrolases which decompose substances taken into the lysosomes both from within and without the cell. Most of the enzyme groups localized in human lysosomes, once biosynthesized and transported to the Golgi apparatus, undergo addition of phosphate groups at the 6-positions of mannose residues at the non-reducing ends of high mannose-type sugar chains, being thereby converted to acidic sugar chain-bearing glycoproteins, and the phosphate groups serve as lysosomal enzyme-specific recognition markers. They are distinguished from other proteins through binding with high affinity mannose-6-phosphate receptors (MPRs), and are carried into prelysosomes where they dissociate from the MPRs in the acidic environment and are then transported to lysosomes (von Figura and Hasilik, Annu. Rev. Biochem., 54, 167-193 (1984)). The binding with mannose-6-phosphate receptors (MPRs) requires that each sugar chain contain one or more mannose-6-phosphate molecules. This lysosomal enzyme-specific phosphate group addition is accomplished by two separate enzyme reactions. W. Canfield et al. have succeeded in cloning the genes for two enzymes (GlcNAc-phosphotransferase, GlcNAc-phosphodiester-GlcNAc'ase) involved in mannose-6-phosphate synthesis (Abstract of the XV International Symposium on Glycoconjugates. Glycoconjugate Journal Vol. 16 No. 4/5 S41 (1999)).

Genetic defects in these lysosomal enzymes, in enzymes involved in the phosphate-addition reaction or in factors contributing to activation or stabilization of the lysosomal enzymes causes a group of diseases characterized by blockage of the enzyme reactions and accumulation of intracellular substrates, such diseases being referred to collectively as "lysosomal disease" (Leroy and DeMars, Science, 157, 804-806 (1967)). Over 30 different types of lysosomal disease are known in humans and together they constitute an important disease group in pediatric and internal medicine. Strategies for developing basic treatments for such diseases have included bone marrow transplantation and gene therapy. Enzyme supplementation therapy using lysosomal enzymes has also been attempted, but poor uptake by target organs has been a major obstacle and at the current time the only satisfactory results have been seen with enzyme supplementation for Gaucher disease.

Gaucher disease results from a mutation in the gene for glucocerebrosidase, a glucosylceramide-degrading lysosomal enzyme, leading to accumulation of its substrate glucosylceramide mainly in bone marrow macrophage-derived cells, and manifested as notable hepatosplenomegaly as well as hematopoietic dysfunction including anemia and hemorrhage. As mentioned above, treatment methods for this disease include enzyme supplementation therapy, which has produced favorable treatment results, but such therapy must be continued for life and the enzyme preparations are extremely expensive. Glucocerebrosidase preparations are produced by modifying the ends of the sugar chains of human recombinant glucocerebrosidase expressed by CHO cells, to a form with the mannose exposed. Since the morbid cells in this disease are primarily macrophages, glucocerebrosidase is presumably transported to lysosomes after being taken up into the cells via mannose receptors on macrophages. Glucocerebrosidase is known to be transported into lysosomes regardless of whether it has mannose-6-phosphate on its sugar chains. It is therefore conjectured that the enzyme is transported to lysosomes by a mannose-6-phosphate receptor (MPR) non-dependent transport mechanism.

However, the deficient enzymes in most other lysosomal diseases are transported to lysosomes by mannose-6-phosphate receptor-mediated systems, and therefore the lysosomal enzymes used for enzyme supplementation therapy must having mannose-6-phosphate-containing sugar chains as the lysosome migration signals necessary for binding with mannose-6-phosphate receptors (MPRs). Addition of mannose-6-phosphate to these lysosomal enzyme chains is therefore a key strategy.

Currently, the reported methods for obtaining lysosomal enzymes include methods of purification from placenta, production methods utilizing cultured cells such as fibroblasts or melanoma cells, recombinant methods using cultured cells such as insect cells or Chinese hamster ovary (CHO) cells, and methods of obtaining the enzymes from transgenic rabbit milk. However, these methods are associated with the disadvantages of 1) low content of lysosomal enzymes with phosphate-added sugar chains and therefore poor uptake efficiency into lysosomes, and 2) low productivity/high culturing cost. Disadvantage 1) therefore requires high-dose administration, while disadvantage 2) leads to high treatment costs. Moreover, production by recombinant methods using yeast cells has not yet been achieved. Thus, enzymes having mannose-6-phosphate on the sugar chains and having high uptake activity into lysosomes have been a desired goal.

One of the lysosomal disease known as Fabry disease is an X-chromosomal genetic disease characterized by reduced α-galactosidase activity and accumulation of its in vivo substrate globotriosylceramide in the body. Fabry disease patients in the classic type of the disease typically suffer extremity pain, cutaneous hemangioma and impaired sweating beginning from youth or adolescence, and exhibit nephropathy or cardiovascular and cerebrovascular disorders with increasing age. In recent years, a relatively mild Fabry disease "subtype" has been identified which is marked by cardiomyopathy in late middle age or thereafter, and it has been reported that such patients may be hidden among patient groups falsely diagnosed with cardiomyopathy.

α-Galactosidase differs from the aforementioned glucocerebrosidase in that it is transported to lysosomes by a mannose-6-phosphate receptor-mediated system. Consequently, it must have mannose-6-phosphate-containing sugar chains in order to be taken up efficiently by the target cells. However, the technology has not existed for mass production of high-purity α-galactosidase with mannose-6-phosphate-containing sugar chains, suitable for use in therapy. For example, the proportion of mannose-6-phosphate sugar chains is thought to be about 20% in fibroblast-derived glycoprotein (α-galactosidase), which has shown superiority as an enzyme supplementation infusion in 9 out of 10 human patients (Pro. Natl. Acad. Sci. USA, 97:365-370 (2000)).

Since the structures of the sugar chains added to proteins differ in yeast and mammalian cells, useful human or other mammalian glycoproteins produced in yeast by genetic engineering methods do not exhibit identical activity as those derived from mammals, or they may have different antigenicities due to the different sugar chains. It has been difficult to produce mammalian glycoproteins in yeast for this reason. Furthermore, while useful phosphate-containing acidic sugar chains having the identical sugar chain structures as are added in human and other mammalian cells would be of benefit in functioning as labeling markers for transport of the glycoproteins to lysosomes in human or other mammalian cells, it is currently difficult to supply such acidic sugar chain-having glycoproteins in uniform, large amounts. The development of such technology has therefore been greatly desired.

The present inventors have previously proposed a method composing using a sugar chain synthesis mutant (ΔOCH1 mnn1) to produce a glycoprotein, allowing the MNN6 gene product to act thereon either in vivo or in vitro to obtain mannose-1-phosphate-added acidic sugar chains, and carrying out acid treatment to obtain mammalian-like sugar chains which are effective as lysosome transport signals (Japanese Unexamined Patent Publication HEI No. 9-135689). However, due to the extreme denaturing conditions used for this method (0.01 N hydrochloric acid, 100° C., 30 minutes), virtually all of the glycoprotein becomes denatured. It has therefore been unsatisfactory as a method for obtaining glycoproteins with physiological activity.

DISCLOSURE OF THE INVENTION

It is an object of the present invention to overcome the aforementioned problems associated with producing glycoproteins in yeast, and thereby to provide a process for producing by using yeast, a useful phosphate-containing acidic sugar chain having the same sugar chain structure as are added in human or other mammalian cells, as well as a glycoprotein having the sugar chain.

As a result of much diligent research directed toward solving the problems described above, the present inventors have found that by using a sugar chain biosynthesis mutant of yeast to obtain a glycoprotein having a sugar chain containing a large number of phosphate and allowing α-mannosidase to act the glycoprotein, it is possible to produce a glycoprotein having a mannose-6-phosphate-containing acidic sugar chain which have no antigenicity, in large amounts at high purity and with its physiological activity retained, wherein the acidic sugar chain can serve as a labeling marker for transporting into lysosomes of mammalian cells, including human cells. It was further found that the resulting glycoprotein with a phosphate-containing acidic sugar chain can be utilized as a drug effective in treatment of human lysosomal enzyme deficiencies, etc. Thus, the present invention was completed.

In other words, the present invention provides a process for producing a glycoprotein with a mannose-6-phosphate-containing sugar chain, characterized by introducing and expressing a gene coding for the target glycoprotein in a sugar chain biosynthesis mutant of yeast which produces highly phosphorylated core sugar chains, and treating the resulting mannose-1-phosphate-added acidic sugar chain-containing glycoprotein with α-mannosidase to remove the mannose moieties.

The invention further provides a glycoprotein with a phosphate-containing acidic sugar chain, including a human lysosomal enzyme, produced by a process for production by using yeast according the present invention.

The invention still further provides a therapeutic composition for lysosomal diseases in which a human lysosomal enzyme produced according to the invention is used.

More specifically, the invention provides the following (1) to (27).

(1) A process for producing an active form of glycoprotein, by using yeast, wherein the active form of glycoprotein has an acidic sugar chain having a mannose-6-phosphate at a non-reducing end.

(2) The process of the foregoing (1), wherein the acidic sugar chain having a mannose-6-phosphate may bind to mannose-6-phosphate receptor.

(3) A process for producing an active form of glycoprotein, by using yeast, wherein the active form of glycoprotein has a high mannose-type sugar chain having a mannose-6-phosphate at a non-reducing end, wherein the high mannose-type sugar chain is shown in the following structural formulas I to VIII:

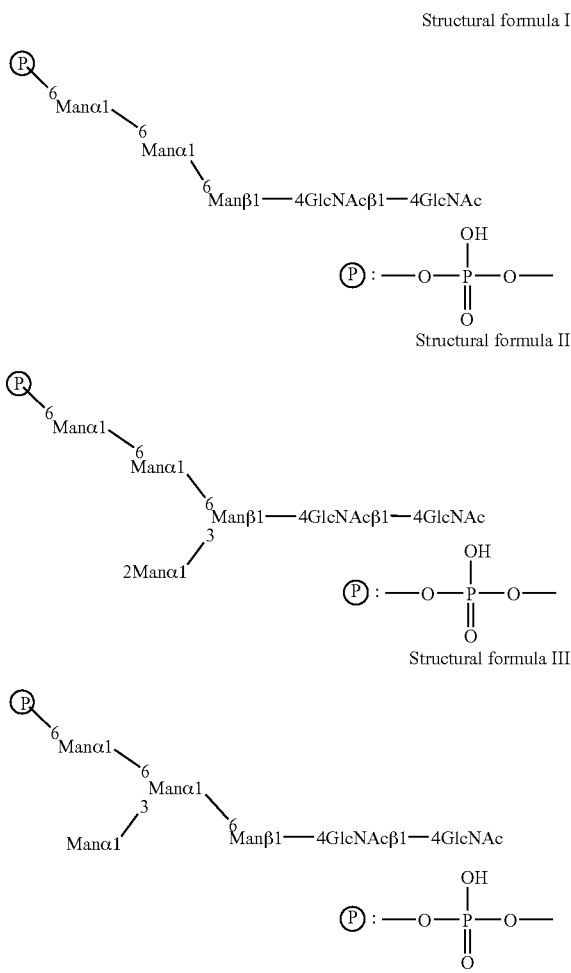

-continued

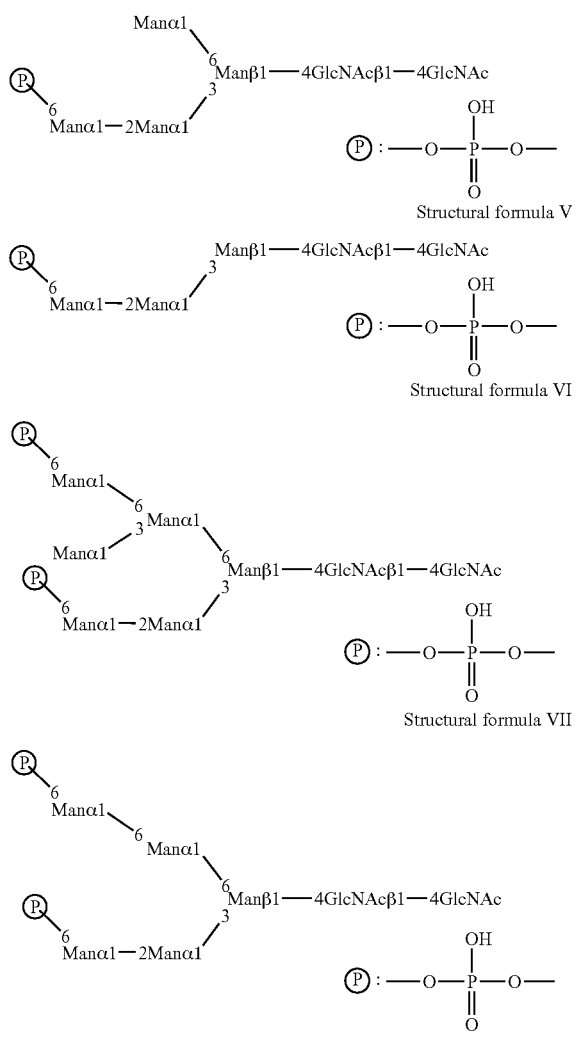

(4) The process of any one of the foregoing (1) to (3), wherein the yeast contains an acidic sugar chain, and at least the α-1,6-mannosyltransferase gene has been disrupted in the yeast strain to be used.

(5) The process of any one of the foregoing (1) to (3), wherein the yeast contains an acidic sugar chain, and at least the α-1,6-mannosyltransferase gene and the α-1,3-mannosyltransferase gene have been disrupted in the yeast strain to be used.

(6) The process of the foregoing (4) or (5), wherein the α-1,6-mannosyltransferase gene is the OCH1 gene of *S. cerevisiae* and the α-1,3-mannosyltransferase gene is the MNN1 gene of *S. cerevisiae*.

(7) The process of any one of the foregoing (1) to (6), wherein the yeast is a highly phosphorylated sugar chain-containing mutant.

(8) The process of the foregoing (7), wherein the yeast is *S. cerevisiae* strain HPY21.

(9) The process of any one of the foregoing (1) to (8), wherein the active form of glycoprotein having an acidic sugar chain having a mannose-6-phosphate is a lysosomal enzyme.

(10) The process of the foregoing (9), wherein the lysosomal enzyme is α-galactosidase.

(11) The process of the foregoing (10), wherein a structural gene for the α-galactosidase is a gene from human.

(12) The process of the foregoing (11), wherein the structural gene for the α-galactosidase has the nucleotide sequence represented by SEQ. ID. No: 5.nucleotide sequence

(13) The process of any one of the foregoing (10) to (12), wherein the yeast producing the α-galactosidase is strain HPY21G.

(14) The process of any one of the foregoing (1) to (13), by allowing α-mannosidase to act on a glycoprotein produced by the yeast as defined in any one of claims 4 to 8 to remove mannose residues from mannose-1-phosphate linkages in sugar chain.

(15) The process of the foregoing (14), wherein the α-mannosidase has an activity which removes mannose residues from mannose-1-phosphate linkages.

(16) The process of the foregoing (14) or (15), wherein the α-mannosidase has an activity which non-specifically breaks down α-1,2-mannoside linkages, α-1,3-mannoside linkages and α-1,6-mannoside linkages.

(17) The process of the foregoing (16), wherein the α-mannosidase activity is exo-type activity, and comprises no endo-type activity.

(18) The process of the foregoing (17), wherein the α-mannosidase is α-mannosidase from *Cellulomonas* bacteria.

(19) The process of the foregoing (18), wherein the *Cellulomonas* bacteria is *Cellulomonas* SO-5.

(20) A glycoprotein, which is produced by yeast and has an acidic sugar chain having a mannose-6-phosphate at a non-reducing end.

(21) The glycoprotein of the foregoing (20), which is a lysosomal enzyme.

(22) The glycoprotein of the foregoing (20) or (21), which is produced by the process of any one of the foregoing (1) to (19).

(23) The glycoprotein of the foregoing (21) or (22), which is α-galactosidase.

(24) The glycoprotein of the foregoing (23), which is α-galactosidase encoded by a gene from human.

(25) The glycoprotein of the foregoing (20), which has a sugar chain with high mannose-type sugar chain structure containing mannose-6-phosphate at a non-reducing end, wherein the sugar chain is shown in the following structural formulas I to VIII:

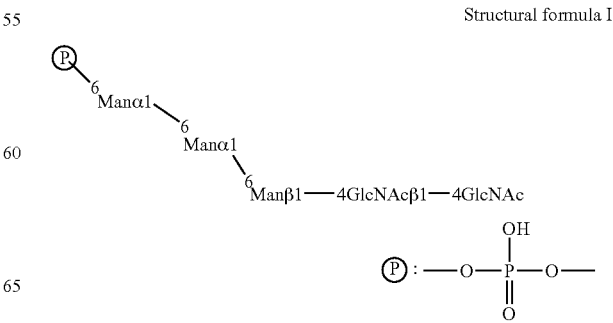

Structural formula I

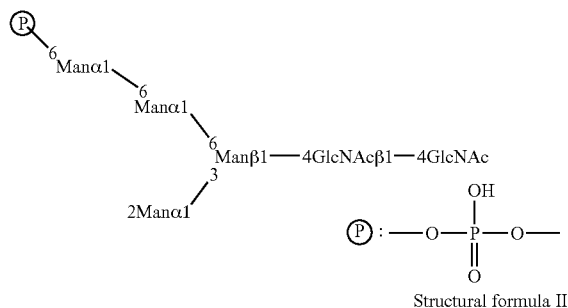

Structural formula II

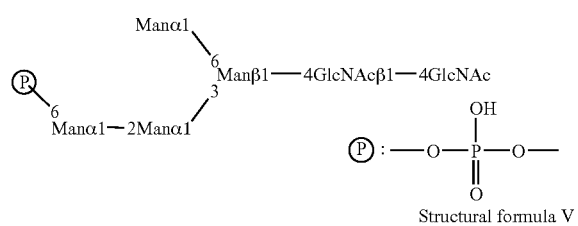

Structural formula III

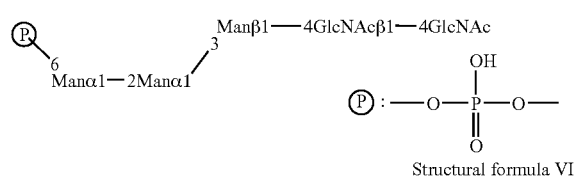

Structural formula IV

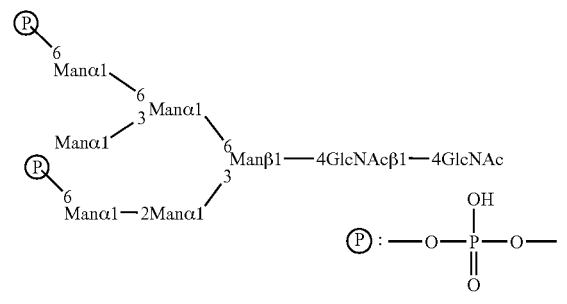

Structural formula V

Structural formula VI

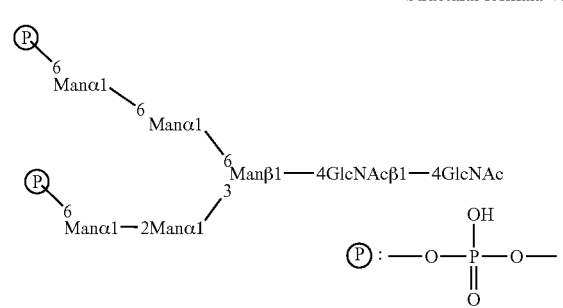

Structural formula VII

(26) A pharmaceutical composition for treatment and/or prevention of lysosomal disease, comprising a glycoprotein according to any one of the foregoing (20) to (25).

(27) The pharmaceutical composition of the foregoing (26), for treatment of Fabry disease, wherein the glycoprotein is human α-galactosidase.

The specification incorporates the matter disclosed in the specification and/or drawings of Japanese Patent Application No. 2001-180907, of which the present application claims the right of priority.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 7 shows the results of structural analysis of α-galactosidase sugar chains purified with an Asahi-Pak NH2-P column from a culture supernatant concentrate of the α-galactosidase gene-introduced strain HPY21G.
1) Sugar chains of α-galactosidase purified from culture supernatant (containing one phosphate molecule in each sugar chain).
2) Sugar chains from the α-mannosidase-treated foregoing 1).
3) Sugar chains from the alkaline phosphatase-treated foregoing 2).
4) Sugar chains from the α-mannosidase and alkaline phosphatase-treated sugar chain moieties of α-galactosidase purified from culture supernatant (containing two phosphate molecules in each sugar chain) treated with α-mannosidase and.

EXPLANATION OF SIGNS

Figure 1:
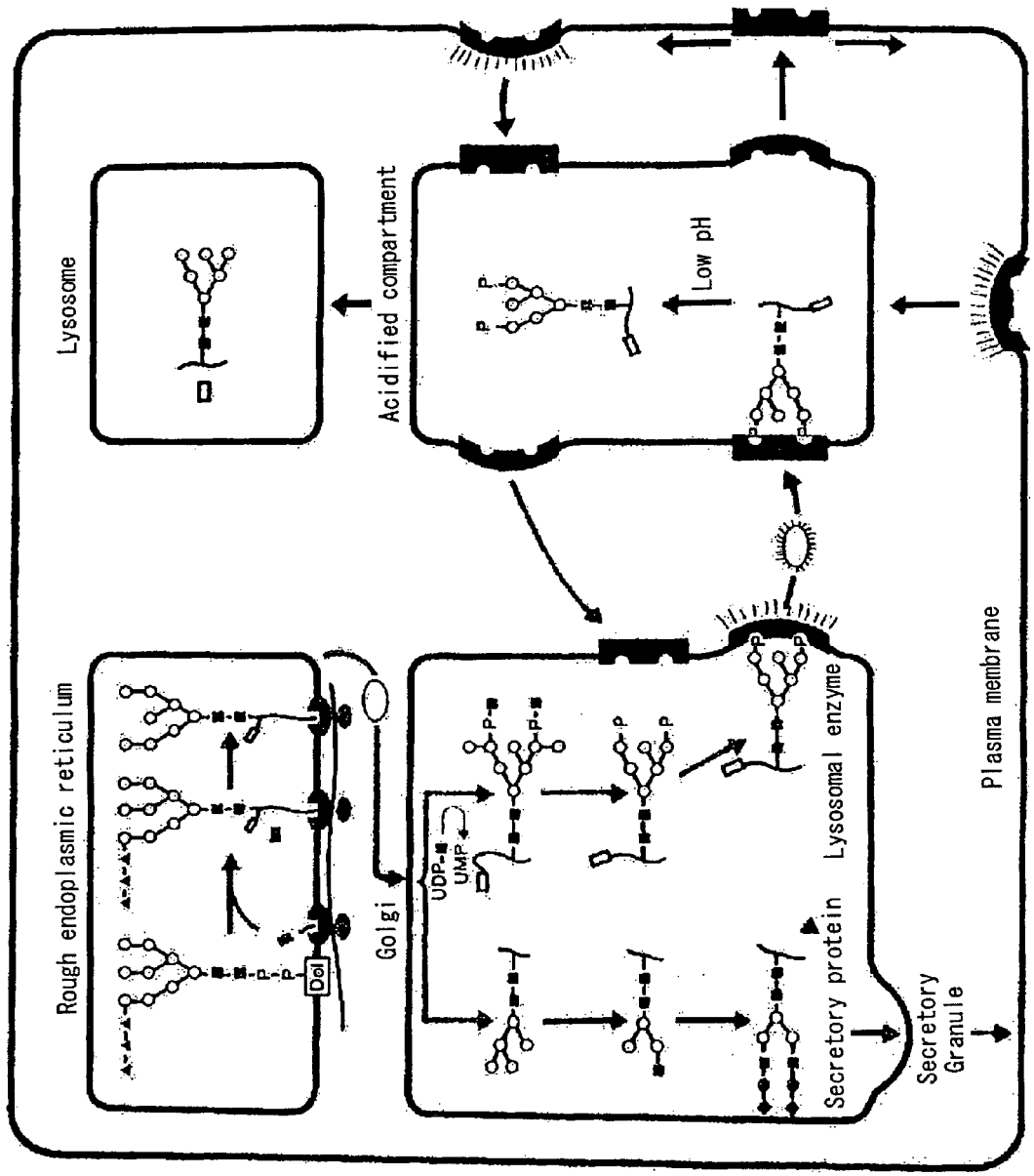
FIG. 1 illustrates the general biosynthesis pathway for N-linked sugar chains in mammals (konfeld et al.).

GlcNAc, GN: N-acetylglucosamine
Man, M: Mannose
PA: 2-aminopyridylated

BEST MODE FOR CARRYING OUT THE INVENTION

The present invention will now be explained in greater detail.

The process for producing glycoproteins having phosphate-containing acidic sugar chains in which the sugar chains can serve as labeling markers for transporting to lysosomes according to the invention comprises basically the following steps.
1) A step of introducing a gene coding for a glycoprotein of interest, into a sugar chain biosynthesis-mutant yeast strain which produces phosphorylated core sugar chains to be used, to express a glycoprotein having mannose-1-phosphate-added acidic sugar chains.
2) A step of α-mannosidase treatment of the obtained mannose-1-phosphate-added acidic sugar chain-having glycoprotein to excise the mannose moieties, thereby yielding a glycoprotein having mannose-6-phosphate-containing sugar chains.

A mutant yeast strain according to the invention having a disruption in an outer chain biosynthetic gene specific to yeast may be prepared in the following manner. First, isolation of DNA gene fragments necessary for disruption of target genes, all of which have been elucidated for their chromosomal positions by the *Saccharomyces cerevisiae* genome project (Goffeau et al., Nature, 387 (suppl.), 1-105 (1997)) may be isolated from any gene fragments surrounding the target genes which can be available from public institutions such as the ATCC (American Type Culture Collection) (ATCC Recombinant DNA materials, 3rd edition, 1993). Alternatively, these may be obtained by extracting genomic DNA from *S. cerevisiae* according to ordinary methods and screening for target genes. Genomic DNA may be extracted from *S. cerevisiae* by, for example, the method of Cryer et al. (Methods in Cell Biology, 12, 39-44 (1975)) or the method of P. Philippsen et al. (Methods Enzymol., 194, 169-182 (1991)).

The target gene is amplified by PCR and then disrupted. The PCR method is a technique allowing in vitro amplification of specific DNA fragments to several hundred thousand-fold within about 2-3 hours, using a combination of sense/antisense primers at both ends of the region of interest, heat stable DNA polymerase and a DNA amplification system. When the technique is employed for amplification of the target gene, 25-30mer synthetic single-stranded DNA as primers and genomic DNA as template are used.

According to the invention, the target gene disruption may be accomplished basically according to the method disclosed by Rothstein in Methods Enzymol., 101, 202-211 (1983). This method entails first cleavage or partial deletion of the target gene DNA on a plasmid and insertion of an appropriate selective marker gene DNA to produce a construct wherein the selective marker is sandwiched between the upstream and downstream portions of the target gene, and then introduction of the construct into yeast cells. Recombination events are occured twice between both ends of the introduced fragment (the DNA construct sandwiching the selective marker) and the homologous portions of the target gene on the chromosome by this procedure, so that the target gene on the chromosome is substituted by the introduced fragment.

Construction of an OCH1 gene-disrupted strain will now be explained as a concrete example. The hisG-URA3-hisG cassette is excised with a restriction endonuclease from the plasmid constructed by Alani et al. having the hisG gene DNA fragment of *Salmonella* linked to both ends of the URA3 gene (Alani et al., Genetics, 116, 541-545 (1987)), and then inserted into the target gene on a plasmid to construct an allele of the disrupted gene. This plasmid is used for substitution for the target gene on the chromosome to obtain a gene-disrupted mutant. The URA3 gene inserted into the chromosome is sandwiched by two of hisG genes, and upon homologous recombination between the hisG sequences and it may be eliminated from the chromosome, along with one copy of hisG. The target gene on the chromosome still retains one copy of the disrupted hisG fragment, but the host cells have the URA$^-$ phenotype. Homologous recombination between the two of the hisG genes can be accomplished with 5-fluoroorotic acid (5-FOA). A ura3 mutant has resistance to 5-FOA (Boeke et al., Mol. Gen. Genet., 197, 345-346 (1984); Boeke et al., Methods Enzymol., 154, 165-174 (1987)), but yeast strains with the Ura3$^+$ phenotype are unable to grow in 5-FOA medium. Thus, the strains exhibiting the resistance trait in 5-FOA-containing medium can be separated, enabling the strains to be again operated by the procedure using the URA3 marker.

The MNN1 gene of this OCH1 gene-disrupted strain may then be disrupted by the same procedure to obtain the intended double mutant strain (Δoch1 Δmnn1).

A yeast Δoch1 mutant is deficient in the initial α-1,6-linked mannose addition reaction which is necessary for addition of mannose outer chains to the core sugar chain of glycoproteins, while a Δmnn1 mutant is deficient in the reaction which adds α-1,3-linked mannose to the non-reducing ends of the core sugar chain and outer chain branches. The double mutant having both mutations (Δoch1 Δmnn1), as already proposed by the present inventors (Japanese Patent Publication No. 3091851), produces the neutral core sugar chain Man8GlcNAc2, with the by-product of mannose-1-phosphate-containing acidic sugar chains in addition to the neutral sugar chain (Proceedings of the 12th Biotechnology Symposium, p.153-157, Oct. 14, 1994, Biotechnology Developmental Technology Research Society).

Figure 2:
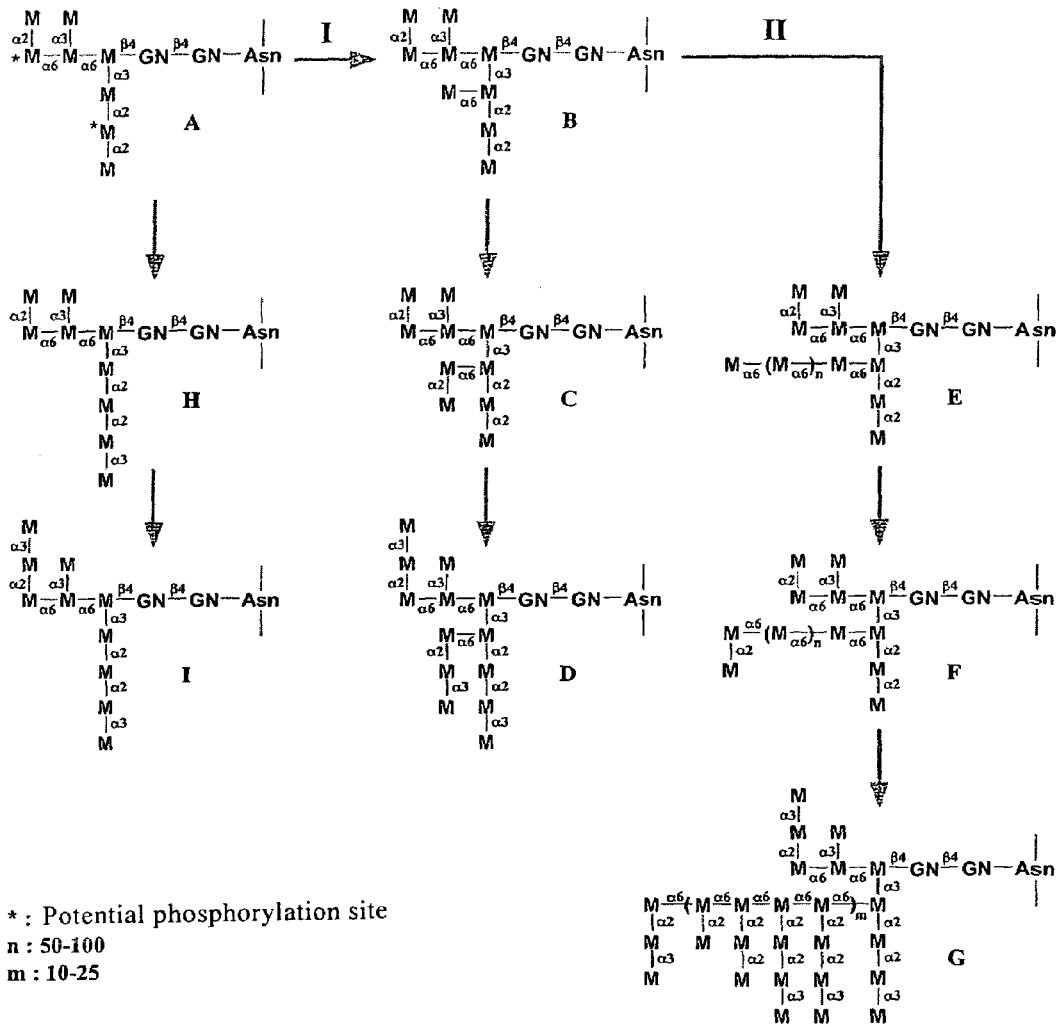
FIG. 2 illustrates the biosynthesis pathway for N-linked sugar chains in yeast (S. cerevisiae).

Yeast strains to be utilized for the invention must have sugar chains having mannose-6-phosphates. Such sugar chains are known to be quite ubiquitous in yeast. *Saccharomyces cerevisiae* genes involved in sugar chain synthesis include the gene which catalyzes the addition reaction of mannose-1-phosphate to the 6-position of mannose (MNN6), indicated by the "*" symbol in the sugar chain structural formula shown in FIG. 2, and the gene which controls the addition of mannose-1-phosphate (MNN4).

Phosphate-containing sugar chains are abundantly detected from the logarithmic growth phase to the late culturing phase (stationary phase). This coincides with the expression pattern of the gene which controls addition of mannose-1-phosphate (MNN4). Enhancing expression of the MNN4 and MNN6 genes may allow breeding of yeast comprising numerous sugar chains with mannose-6-phosphate.

*Saccharomyces cerevisiae* KK4 is a strain which has a mutation in the promoter region of the MNN4 gene and which constitutively expresses the MNN4 gene. It therefore comprises numerous phosphorylated sugar chains. It was therefore considered suitable for production of glycoproteins having a mannose-6-phosphate.

The method of introducing the DNA into cells and transforming the cells therewith may be ordinary methods, for example, infection of E. coli cells with phage vectors or the like, for efficient incorporation of the DNA into the host cells. As a method for transforming yeast using plasmids, there may be employed a method of incorporating the plasmids by treatment with a lithium salt to produce a condition of natural uptake of DNA, or a method of electrically introducing DNA into the cells (Becker and Guarente, Methods Enzymol., 194, 182-187 (1991)).

The isolation, purification, etc. of the DNA for the procedure described above may also be carried out according to ordinary protocols, and in the case of E. coli for example, the DNA may be extracted by the alkali/SDS method and ethanol precipitation, and the DNA subsequently purified by RNase treatment, PEG precipitation and the like. The DNA sequence of the gene may be determined by a common method such as, for example, the dideoxy method (Sanger et al., Proc. Natl. Acad. Sci., USA, 74, 5463-5467 (1977)). DNA nucleotide sequences can be easily determined utilizing commercially available sequencing kits and the like.

In order to produce a glycoprotein of a different species having the aforementioned sugar chains, a gene may be constructed comprising the gene (cDNA, etc.) coding for a target glycoprotein linked downstream from a promoter capable of expression in yeast, and the construct incorporated into the yeast mutants described above as host cells by homologous recombination, or the gene may be introduced into a plasmid and used to transform the host cells to produce transformants, which may then be cultured by a publicly known method to allow collection of the target glycoprotein produced either intracellularly or extracellularly by the yeast.

In this case, it is sufficient if the gene coding for the target glycoprotein has the same translated amino acid sequence. Because humans have different codon usage than yeast, human-derived genes are usually poorly expressible in yeast. Thus, higher expression may be expected if a gene is synthesized to have its codon usage converted to the yeast system. Basically, the gene used must be a gene coding for the same amino acid sequence as the human-derived enzyme, because an enzyme of a different species will raise concerns regarding antigenicity.

Culturing of the yeast mutant may be carried out by ordinary methods commonly employed for culturing of yeast. There may be used synthetic media (including nitrogen sources, carbon sources, inorganic salts, amino acids, vitamins, etc.) containing various culturing components available, for example, from Difco Laboratories, and lacking amino acids which may be supplied depending on the markers necessary for replication and retention of plasmids (Sherman, Methods Enzymol., 194, 3-57 (1991)). Incorporation of the foreign gene into a chromosome instead of onto a plasmid will prevent elimination of the gene and will thus allow culturing in ordinary nutrient-rich media.

Common protein isolation and purification methods may be employed for isolation and purification of the glycoprotein from the cultured product (culture solution or cultured cells). For example, in the case of a glycoprotein present in the cells, the cells are collected by centrifugal separation after completion of culturing and suspended in an aqueous buffer solution, and then the cells are disrupted with an ultrasonic disrupter, French press, Manton-Gaulin homogenizer, Dynomill or the like, and the cell-free extract is centrifuged to obtain the supernatant. In the case of a glycoprotein present in the culture supernatant, the cells are separated by centrifugal separation after completion of culturing, and then concentrated by ultrafiltration, salting out or the like. The subsequent procedures may be carried out by ordinary protein isolating and purifying methods, such as solvent extraction, salting out with ammonium sulfate or the like, desalting, precipitation with organic solvents, anionic-exchange chromatography using diethylaminoethyl (DEAE) Sepharose or the like, cationic-exchange chromatography using sulfopropyl (SP) Sepharose (by Pharmacia) or the like, hydrophobic chromatography using Phenyl Sepharose or the like, gel filtration using a molecular sieve with Sephacryl or the like, affinity chromatography using a group-specific carrier, lectin ligand, metal chelate or the like, chromatofocusing or electrophoretic methods such as isoelectric electrophoresis, either alone or in combination, to obtain a purified product.

Affinity chromatography was successfully carried out according to the invention to separate α-galactosidase having phosphorylated sugar chains from α-galactosidase having no phosphorylated sugar chains. Specifically, Blue Sepharose chromatography was used to separate target glycoproteins. The affinity ligand used for Blue Sepharose is Cibacron Blue F3GA, a type of chlorotriazine pigment, and it may be possible to apply methods of purifying glycoproteins with mannose-6-phosphate-containing acidic sugar chains by affinity chromatography using as ligands such pigments which allow separation of phosphorylated sugar chains.

The phosphate-dependent differences in charges of sugar chains may be utilized in ion-exchange, chromatofocusing or isoelectric electrophoresis to purify and concentrate glycoproteins having mannose-6-phosphate-containing sugar chains, and more specifically, the following yeast-specific glycoproteins having mannose removed from mannose-1-phosphate.

Also, the difference in binding specificity of Concanavalin A (ConA), known as a mannose-recognizing lectin, may be utilized: yeast-derived glycoproteins with non-phosphorylated sugar chains have their sugar chains cleaved by α-mannosidase, and therefore reduced or eliminated affinity for ConA. On the other hand, since mannose-6-phosphate is not recognized as the substrate in the case of phosphate-containing sugar chains, no further cutting of the sugar chains occurs and the affinity for ConA is not reduced. This may be utilized to obtain a pure lysosomal enzyme sample with high biological activity, i.e. high uptake activity into cells, and more specifically high binding activity with mannose-6-phosphate receptors, which is suitable as a highly functional pharmaceutical product.

The α-mannosidase used to remove yeast-specific mannose according to the invention is not particularly limited so long as it degrades mannose-1-phosphate linkages, has exotype activity, acts on a glycoprotein and acts in a pH range in which the glycoprotein to be treated is stable. Such α-mannosidases have a wide range of substrate specificity, acting on α-1,2, α-1,3 or α-1,6-linked mannoside linkages, while also acting on synthetic substrates such as p-nitrophenyl-α-mannopyranoside or 4-methylumbelliferyl-α-mannopyranoside. Possible α-mannosidases to be used include Jack Bean α-mannosidase and yeast vacuole-derived mannosidase. However, Jack Bean α-mannosidase has relatively low enzyme activity for glycoprotein sugar chains and requires a prolonged reaction, while its optimum pH is also slightly toward the acidic end (pH 4.5). Thus, because proteins which are unstable in slight acidity may be inactivated, this enzyme is considered unsuitable for obtaining structural stable proteins by removal of sugar chains from glycoproteins. It is therefore necessary to provide a novel α-mannosidase which has stronger enzyme activity, is easily purifiable and can act at neutral pH in which glycoproteins are stable. The α-mannosidase produced by the Cellulomonas SO-5 strain obtained by the present inventors satisfies these conditions, and may be considered an effective enzyme for the present invention. The aforementioned *Cellulomonas* SO-5 strain was deposited internationally as FERM BP-7628 on Jun. 12, 2001 at the International Patent Organism Depositary, National Institute of Advanced Industrial Science and Technology, Tsukuba Central 6, 1-1-1 Higashi, Tsukuba, Ibaraki, Japan.

The enzyme-producing yeast of the invention is not particularly restricted so long as it eventually produces mannose-6-phosphate upon treatment with α-mannosidase and can yield sugar chains with no antigenicity. For example, *Pichia pastoris* is a methanol yeast which produces a glycoprotein with mannose-1-phosphate-containing sugar chains, and treatment with α-mannosidase should produce sugar chains equivalent to those of budding yeast.

Furthermore, the lysosomal enzyme produced according to the invention is not particularly limited to α-galactosidase. For example, the genes for β-hexosaminidase A which is a treatment agent for Tay-Sachs disease, β-hexosaminidase A and B which are treatment agents for Sandhoff disease, galactocerebrosidase which is a treatment agent for Krabbe disease, α-iduronidase which is a treatment agent for Hurler disease, β-glucuronidase which is a treatment agent for Sly disease, α-fucosidase which is a treatment agent for fucosidosis or α-N-acetylgalactosaminidase which is a treatment agent for Schindler disease and Kanzaki disease, may be expressed and purified in the same manner for applications as drugs for treatment and/or prevention of various lysosomal diseases.

In the case of α-galactosidase, it may be used as a treatment agent for Fabry disease by administering the α-galactosidase in the amount necessary for treatment. Here, an amount necessary for treatment means an amount of α-galactosidase which significantly alleviates the symptoms of Fabry disease. α-Galactosidase has a plurality of mannose-6-phosphate-containing sugar chains and exhibits activity of binding to mannose-6-phosphate receptors, as specified according to the present invention. The α-galactosidase is administered as a pharmaceutical composition containing a standard medically acceptable stabilizer, isotonic solution, etc., and for example, it may be administered by intravenous infusion by an ordinary method. The α-galactosidase produced according to the invention contains mannose-6-phosphate-containing sugar chains in an amount equivalent to or greater than purified enzyme samples obtained from human tissue and recombinant enzyme samples produced by cultured animal cells or transgenic animals and is therefore able to exhibit its effect with lower doses, while it avoids contamination by viruses and the like which is a problem with drugs employing animal tissue, so that a stable and highly functional pharmaceutical composition can be provided.

According to the invention, the pharmaceutical composition may comprise, in addition to the glycoprotein, suitable pharmaceutically acceptable stabilizers, buffers, excipients, binders, disintegrators, correctives, coloring agents, aromas and the like, and may be prepared in the form of an injection, tablets, capsules, granules, fine granules, powder or the like. The dosage form of the pharmaceutical composition of the invention may be either oral administration or parenteral administration, such as intravenous injection, intramuscular injection, etc. The dosage will depend on the age, body weight and symptoms of the patient and the route of administration, but it is preferably in the range of 1-10 mg per dose in the case of oral administration and in the range of 10-50 mg per dose in the case of parenteral administration, in terms of the amount of active ingredient for one adult.

The invention is not limited to treatment agents for lysosomal disease, as it may also be utilized as a technique for transport of glycoproteins to lysosomes. Such a technique may be employed for research on lysosomal enzyme transport mechanisms or mechanisms for waste product degradation in lysosomes, thus leading to further advancement of research in the relevant field.

The present invention will now be explained in greater detail through the following examples, while the examples are not intended to limit the technical scope of the invention in any way.

EXAMPLE 1

Construction of the Sugar Chain Biosynthesis Double Mutant Yeast Containing Highly Phosphorylated Sugar Chains (*Saccharomyces cerevisiae* Δoch1 Δmnn1 Strain)

A cassette (HUH) in which *Salmonella* hisG gene was linked to both ends of URA3 gene by direct repeat was excised with BglII and BamHI from pNK51, which has been already reported (Alani et al., Genetics, 116, 541-545 (1987)), and was inserted into BamHI site in *Escherichia coli* plasmid pSP73. This plasmid was designated as pSP73-HUH.

The OCH1 gene is located on yeast chromosome 7, and the DNA nucleotide sequence of the OCH1 gene is registered in the GenBank database under the accession No. D11095 (Nakayama et al., EMBO J., 11, 2511-2519 (1992)). The previously constructed OCH1 gene-disrupting vector poch1::LEU2-1 (Nakayama et al., EMBO J., 11, 2511-2519 (1992)) was cleaved with SalI and HindIII to excise the region containing Δoch1::LEU2, and this was used to transform the highly phosphorylated sugar chain-producing yeast, *Saccharomyces cerevisiae* KK4 strain (MATa URA3 his1 or his3 trp1 leu2 gal80; Nogi et al., Mol. Gen. Genet., 195, 29-34 (1984)) by the lithium acetate method (Ito et al., J. Bacteriol., 153, 163-168 (1983)). Strains having Δoch1 disruption exhibit hypotonic sensitivity. Therefore, the transformed cells were spread on a plate containing 0.3 M KCl in SD-Ura medium (2% glucose, 0.67% Yeast Nitrogen Base w/o amino acids (Difco), nucleobases excluding uracil, and a mixture of amino acids (20-400 mg/L)), and cultured at 30° C. for 2 days to obtain a transformant.

Genomic DNA was prepared from the transformant, and confirmed the integration of a uracil marker into the Δoch1 region of the chromosome by PCR. This transformant was designated as HPY11 strain.

MNN1 gene is located in the vicinity of chromosome 5 centromere of yeast, and the DNA nucleotide sequence of MNN1 gene is registered in the GenBank database under the accession NO. L23753 (Yip et al., Proc. Natl. Acad. Sci. USA, 9, 2723-2727 (1994)). 3' region of MNN1 gene was amplified by PCR using Primer A (GGATCCGAAGAAAACCTAATA-CATTGAAGT: SEQ ID NO: 1) and Primer B (GCATGC-CCTTTGGTTTAATATAAATCTCCGGAGTGC: SEQ ID NO: 2), and 5' region of the same was amplified by PCR using Primer C (GCATGCTACATAACTCCAATCAGCAG-CAAATATGTC: SEQ ID NO: 3) and Primer D (GCGGC-CGCGTGTTCTGTTCGGGTAACGTTTAAACCAAT: SEQ ID NO: 4). The obtained DNA fragments were incorporated into SphI site in plasmid pHYH carrying HIS3 marker to construct pHYHΔmnn1. In order to disrupt the MNN1 gene using the HUH cassette, the 1.8 kb SphI fragment was obtained from pHYHΔmnn1 and inserted into the SphI site of pSP73-HUH to construct pSP73-Δmnn1::HUH. This plasmid was cleaved at the NotI site to be linearized, and used to transform strain HPY11 by the lithium acetate method. After transformation, the cells were spread on plate containing 0.3 M KCl in SD-Ura medium, and cultured at 30° C. for 2 days to obtain a transformant.

Genomic DNA was prepared from the transformant, and confirmed the integration of a uracil marker into the MNN1 region of the chromosome by PCR. This transformant was designated as HPY22 strain. From this strain, selection was carried out in 0.3 M KCl and 5-FOA in YSD medium (1% yeast extract, 2% glucose, adenine (40 mg/L), uracil (20 mg/L)), and thereby URA3 gene deficient strain was obtained. In the same manner as described above, mnn1 disrupted strain lacking URA3 gene was confirmed by PCR. This strain, containing Δoch1::LEU2 Δmnn1::hisG, was designated as the highly phosphorylated sugar chain-containing double mutant yeast strain *Saccharomyces cerevisiae* HPY21.

EXAMPLE 2

Introduction of α-Galactosidase Gene into the Δoch1 Δmnn1 Double Disrupted Strain The sequence of the human α-galactosidase gene is registered in the GenBank database under as NM000169 (Nucleic Acids Res. 17 (8), 3301-3302 (1989)). The previously reported pCXN2 (in Ishii et al., Hum. Genet. 89, 29-32 (1992)) was cleaved with EcoRI to excise the cDNA region for human α-galactosidase (−16 to +1290; SEQ ID No: 5). For the purpose of expression in yeast, it was then inserted into the EcoRI site of the yeast expression vector plasmid YEp352-GAP. The resulting plasmid was designated as YEp352-GAP-GLN. The cDNA region for human αgalactosidase including the promoter and terminator regions was then excised with BamHI from the plasmid, and inserted into the BamHI site of the integration vector pRS404. After cleaving this plasmid pRS-GLN-4 with Bst1107I, it was used to transform the *S. cerevisiae* HPY21 strain constructed in Example 1. The transformation was carried out by the lithium acetate method. After transformation, the cells were spread on a plate containing 0.3 M KCl in SD-Trp medium (2% glucose, 0.67% Yeast Nitrogen Base w/o amino acids (Difco), a mixture of nucleobases/amino acids excluding tryptophan (20-400 mg/L)), and cultured at 30° C. for 2 days to obtain transformant *S. cerevisiae* HPY21G.

The *S. cerevisiae* HPY21G strain was then cultured in 5 ml of 0.3 M KCl in YPAD medium (2% polypeptone, 1% yeast extract, 2% glucose, adenine (40 mg/L)) at 30° C. for 3 days, and then centrifuged to collect the culture supernatant. An approximately 5-fold concentrate was obtained as a crude enzyme solution with ultrafilter membrane (Ultrafree C3LGC (molecular weight cut-off: 10,000), Millipore). The crude enzyme solution was denatured with SDS Sample Buffer and subjected to Western blot analysis according to an ordinary procedures. The Western blot analysis was carried out using rabbit anti-α-galactosidase antibody as the primary antibody and anti-rabbit Ig antibody/alkaline phosphatase complex as the secondary antibody, and detection was carried out by X-ray film exposure using a CDP-Star system (Pierce).

Figure 5:
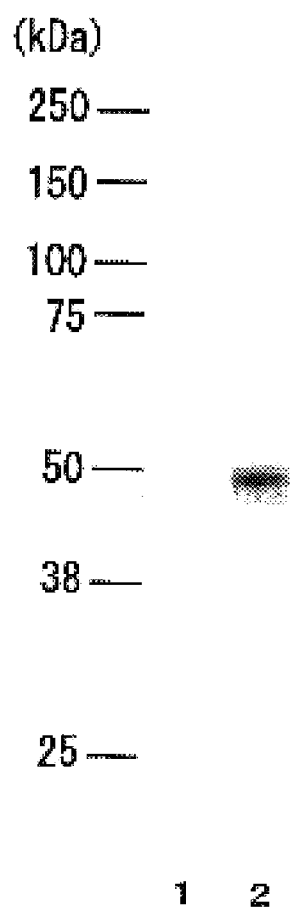
FIG. 5 is a photograph of Western blot analysis for a culture supernatant of the α-galactosidase gene-introduced strain HPY21G.
1) Vector alone-introduced strain (HPY21)
2) α-Galactosidase gene-introduced strain (HPY21G)

As a result, absolutely no signal was detected with the control strain HPY21, while a signal was confirmed at approximately 50 kDa molecular weight in the culture supernatant of the transformant HPY21G (FIG. 5).

The α-galactosidase enzyme activity in the crude enzyme solution was assayed. After adding 10 μl of enzyme solution to 60 μl of 5 mM 4-methylumbelliferyl-D-galactopyranoside in 0.15 M acetate buffer (pH 4.6), the mixture was allowed to react at 37° C. for 30 minutes. 700 μl of 0.2 M glycine/sodium hydroxide buffer (pH 10.7) is added to the mixture to stop the reaction. The reaction mixture was then subjected to measurement using a fluorophotometer (Ex: 365 nm, Em: 450 nm). As a result, the fluorescence was clearly increased when the crude enzyme solution derived from strain HPY21G was used as the enzyme source, compared to the crude enzyme solution derived from the control strain HPY21 (Table 1).

TABLE 1

| Enzyme activity of α-galactosidase in crude enzyme solution | |
| --- | --- |
| Strain | Activity (nmol/min/ml) |
| HPY21 (Control) | 0 |
| HPY21G (α-galactosidase gene-introduced strain) | 24.8 |

EXAMPLE 3

Purification of α-Galactosidase from Culture Supernatant of α-Galactosidase Gene-Introduced Strain, and Analysis of Sugar Chain Structure of the Purified Enzyme The α-galactosidase gene-introduced strain HPY21G was cultured and a crude enzyme solution thereof prepared in the same manner as Example 2. The crude enzyme solution was adjusted to pH 4.5 and subjected to column chromatography with Blue Sepharose CL-6B (Pharmacia). After washing with sodium acetate buffer (pH 4.5), elution was performed with 4 M NaCl in MES buffer (pH 6.0). Upon assaying the enzyme activity of each fraction, α-galactosidase activity was detected in both the column flow-through fraction and the eluted fractions. Each fraction was applied to ConA Sepharose. After washing with 0.15 M sodium chloride, 0.5 mM calcium chloride and 0.5 mM manganese chloride in MES buffer (pH 6.0), the α-galactosidase was eluted with 0.15 M sodium chloride, 0.5 mM calcium chloride, 0.5 mM manganese chloride and 0.2 M α-methylmannoside in MES buffer (pH 6.0). The eluted fractions were further applied to a MonoQ. After washing with MES buffer (pH 6.0), gradient elution was performed with 1 M NaCl in MES buffer. The fraction with strong enzyme activity was dialyzed and then concentrated to obtain a purified α-galactosidase preparation.

The obtained α-galactosidase was treated with enzyme to obtain the asparagine-linked sugar chains. The lyophilized product of the sugar chains was dissolved in 100 μl of N-glycosidase F buffer (0.5% SDS and 0.35% 2-mercaptoethanol in 0.1 M Tris-HCl buffer (pH 8.0)), and the solution was boiled for 5 minutes. After cooling down to room temperature, 50 μl of 7.5% Nonidet P-40, 138 μl of $H_2O$ and 12 μl of N-glucosidase F (Behringer) were added. The mixture was then treated at 37° C. for 16 hours. Desalting was performed with a BioRad AG50W-X8 column to obtain a sugar chain preparation.

The following procedure was carried out for fluorescent labeling (pyridylamination, hereinafter abbreviated to "PA") of the resulting sugar chains. The sugar chain preparation was concentrated to dryness, and then 40 μl of a coupling reagent (a solution of 552 mg of 2-aminopyridine in 200 μl of acetic acid) was then added thereto. The mixture was hermetically sealed and treated at 90° C. for 60 minutes. After cooling down to room temperature, 140 µl of a reducing reagent (a solution of 200 mg of borane/dimethylamine complex in 50 µl of $H_2O$ and 80 µl of acetic acid) was added. The mixture was then hermetically sealed and treated at 80° C. for 80 minutes. After the reaction, gel filtration was performed with a TOYO-PEARL HW-40F (TOSOH) to remove unreacted 2-aminopyridine. The sugar chain fraction was filtered through a 0.22 µm filter, and thus a PA-oligosaccharide preparation was obtained.

Figure 6:
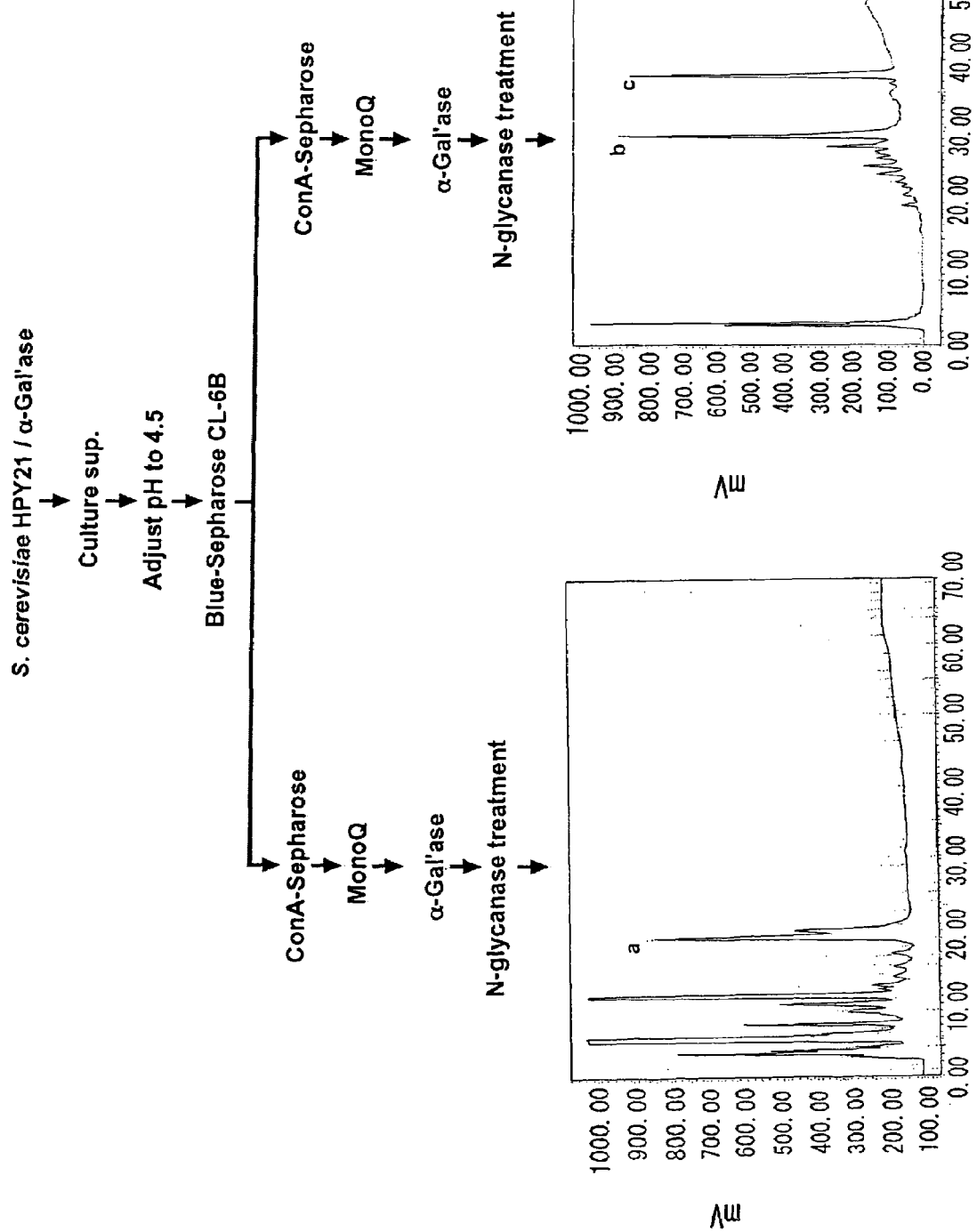
FIG. 6 shows the results of structural analysis of α-galactosidase sugar chains separated by Blue Sepharose from a culture supernatant concentrate of the α-galactosidase gene-introduced strain HPY21G.

The sugar chain structure was analyzed according to a method proposed by the present inventors (Japanese Unexamined Patent Publication No. 9-135689). With HPLC using an amino column it is possible to separate PA-oligosaccharides based on their chain lengths, and also to separate phosphorylated sugar chains from non-phosphorylated sugar chains due to the delay in elution time caused by strong adsorption of phosphate onto amino column. an Asahipak NH2P-50 amino column (4.6×250 mm) was used as a column. The solvents used were 200 mM acetic acid-triethylamine (pH 7.2) as solvent A and acetonitrile as solvent B. The column was equilibrated beforehand by flowing through 30% solvent A and 70% solvent B at a flow rate of 1.0 ml/min. Elution was performed at a flow rate of 1.0 ml/min, at a linear gradient beginning with 70% solvent B up to 20% solvent B in 50 minutes, and then the PA-oligosaccharides were eluted. The results are shown in FIG. 6. The sugar chains prepared from α-galactosidase in the Blue Sepharose elution fraction eluted at near 20 minutes (peak A), while the sugar chains prepared from α-galactosidase in the Blue Sepharose flow-through fraction eluted at near 30 minutes (peak B) and at near 38 minutes (peak C).

Peak A eluted at the same point as Man8GlcNAc2-PA. This indicates that it is a sugar chain having a Man8GlcNAc2 structure with no phosphate addition. The elution points of peaks B and C indicated that peak B was a sugar chain with one molecule of mannose-1-phosphate and peak C was a sugar chain with two molecules of mannose-1-phosphates. The structures for peaks B and C were further confirmed by alkaline phosphatase treatment according to the method described below.

These results demonstrated that the yeast sugar chain biosynthesis double mutant containing highly phosphorylated sugar chains strain HPY21G, in which α-galactosidase gene has been introduced, produces α-galactosidase having sugar chains, which are the phosphate-added high-mannose type sugar chains (Man-P)2-Man8GlcNAc2 and (Man-P)-Man8GlcNAc2 and the high-mannose type sugar chain Man8GlcNAc2, in a ratio of about 1:1:1.

It was also shown that Blue Sepharose chromatography can separate α-galactosidase with phosphorylated sugar chains and α-galactosidase without phosphorylated sugar chains.

Figure 3:
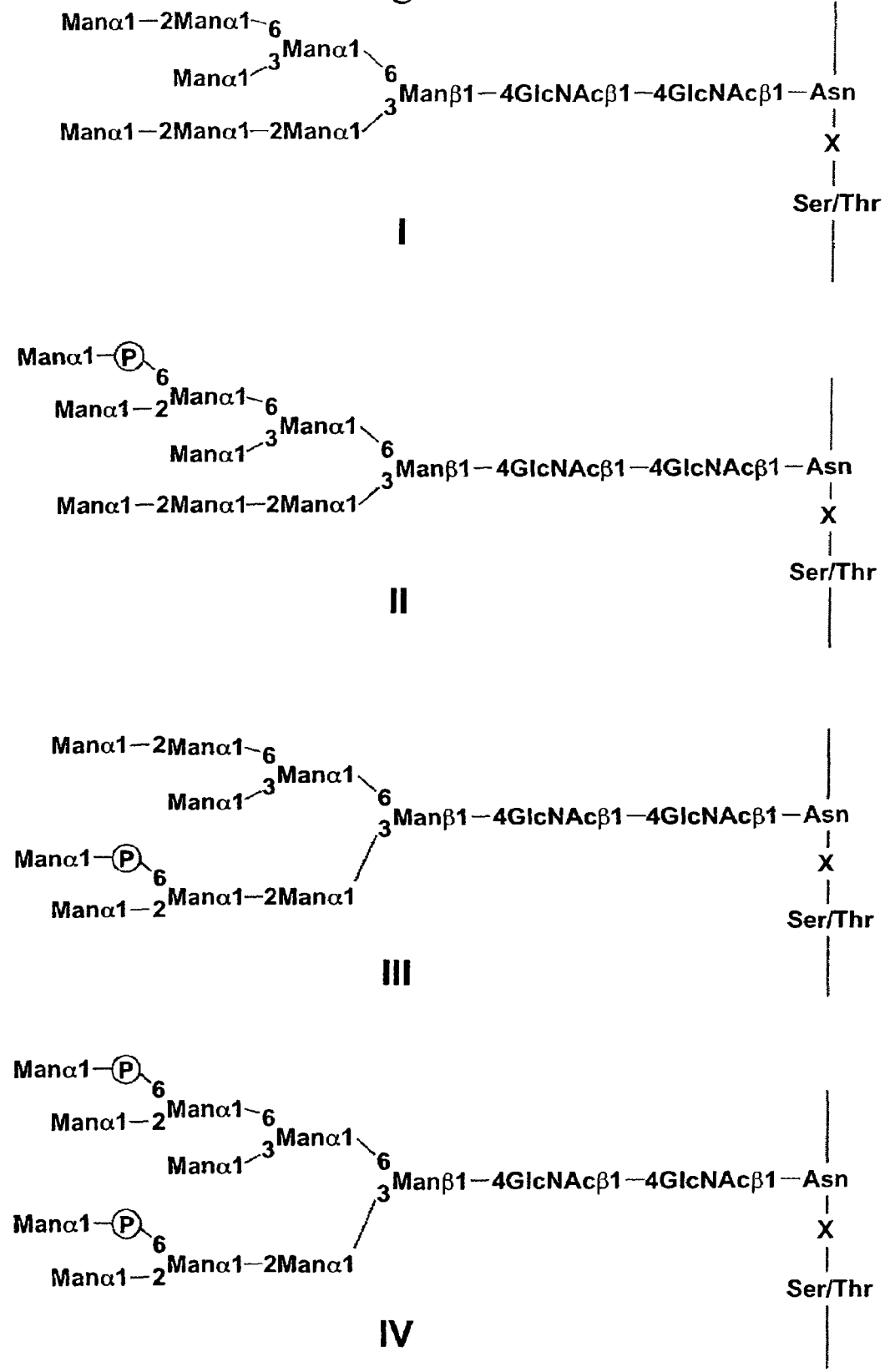
FIG. 3 shows the structures of the core sugar chains and the acidic sugar chains produced by yeast strain HPY21 (Δoch1 Δmnn1).
Figure 4:
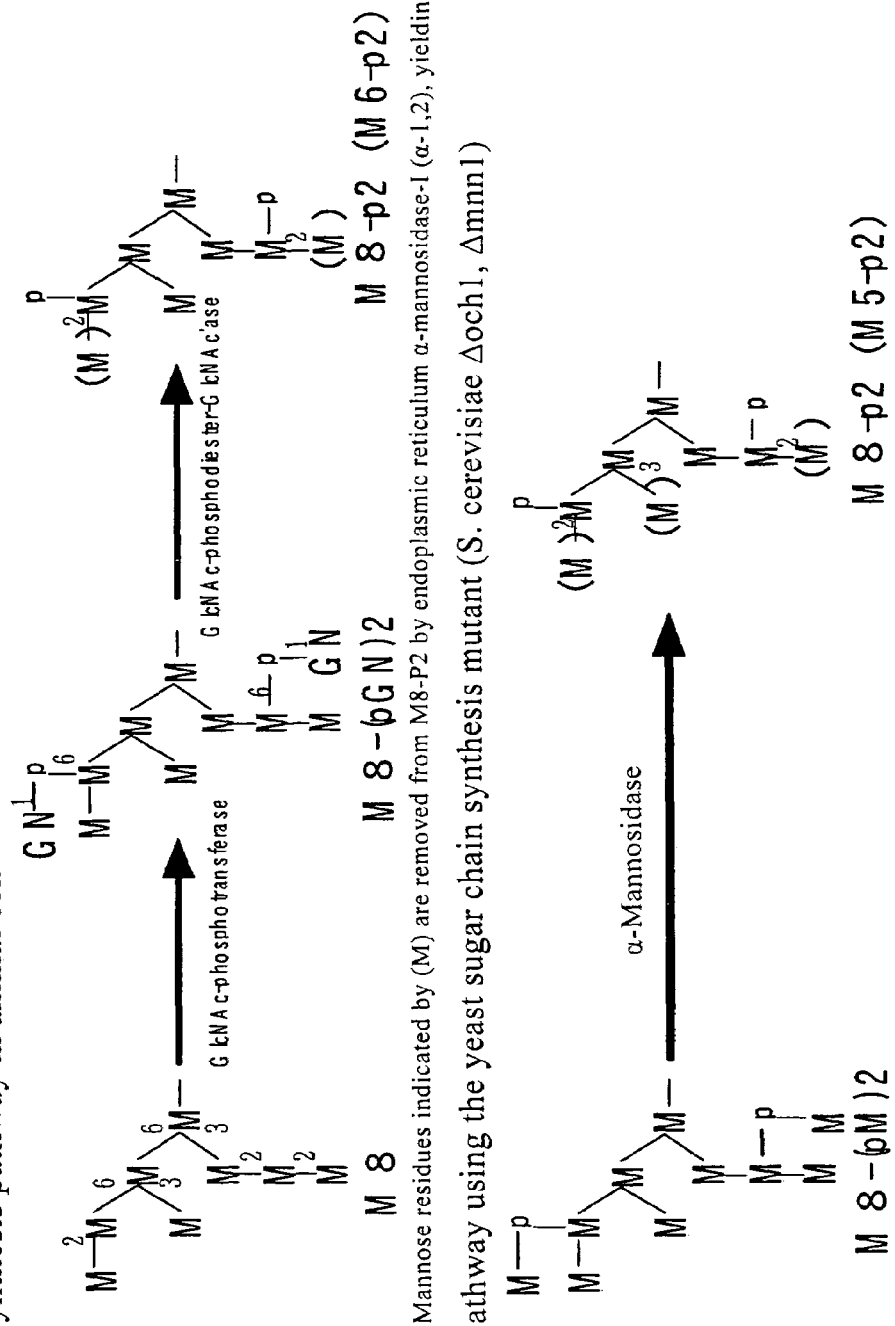
FIG. 4 shows a strategy diagram according to the invention.

The reaction products (peaks B and C) (FIG. 6) were analyzed to determine whether they were mannose-1-phosphate-added products. First, the compounds whose structures had already been confirmed by NMR (FIG. 3, Structural Formulas II, III and IV) were subjected to HPLC, and thus the compounds with Structural Formulas II and III eluted at near 30 minutes. It was therefore concluded that peak B which appeared in the activity assay also contained sugar chains having one molecule of mannose-1-phosphate. The elution point for Structural Formula IV having two molecules of mannose-1-phosphates was considerably later than this peak, and therefore peak C was assumed to be a sugar chain having two molecules of mannose-1-phosphates.

Figure 7:
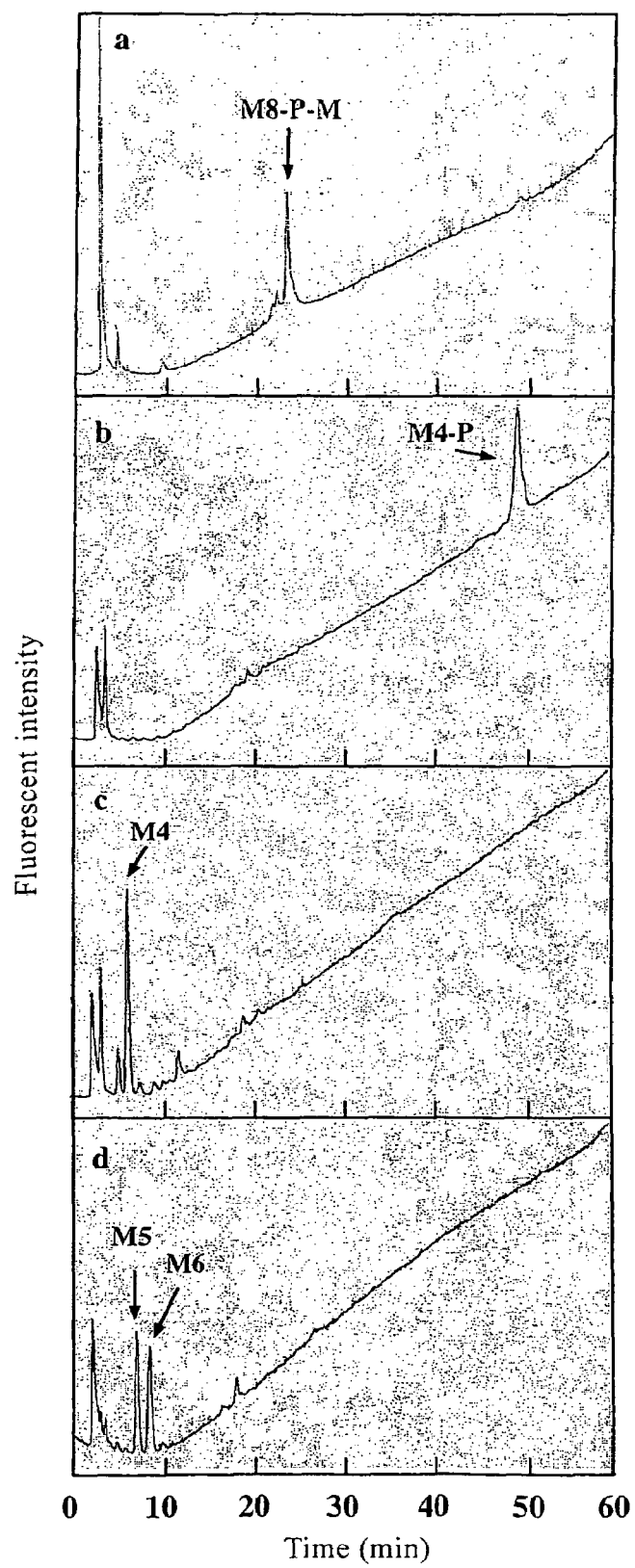

In order to directly confirm that peak B represented sugar chains with one molecule of mannose-1-phosphate, peak B was fractionated and digested with Jack Bean α-mannosidase to excise the mannose moieties from the mannose-1-phosphate residues. The solvent in the fractionated peak was removed by freeze-drying, and then 60 mU of Jack Bean α-mannosidase (Seikagaku Corp.) in sodium acetate buffer (pH 4.5) was added for overnight at 37° C. As a result, as shown in FIG. 7b, the elution was at a later point than the original sugar chains. Upon alkaline phosphatase treatment, the elution occurred at the same point as Man4GlcNAc2-PA, indicating that the sugar chains treated with Jack Bean α-mannosidase had the structure PO4-Man4GlcNAc2-PA. Peak C was also subjected to Jack Bean α-mannosidase treatment and alkaline phosphatase treatment in the same manner, and the elution occurred at a later point, as in peak B. Furthermore, it was clearly demonstrated that peak C represented acidic sugar chains shown in Structural Formula IV in FIG. 3, since it had been eluted at the same point as Man6GlcNAc2-PA when the alkaline phosphatase treatment alone had been carried out (FIG. 7d).

The results described above indicated that the tested strain is suitable for production of mannose-1-phosphate-added acidic sugar chain-having glycoproteins, as precursors of effective mannose-6-phosphate-added acidic sugar chain-having glycoproteins.

REFERENCE EXAMPLE 1

Activity Assay of *Cellulomonas* SO-5-Derived α-Mannosidase Enzyme and Contaminating Enzymes While screening for novel α-mannosidase-producing bacteria from soil bacteria, the present inventors assayed mannan-degrading activity by a reaction using α-mannan as the substrate, and subsequent measurement of the reducing ability of the free sugars. Specifically, the reaction was conducted in a reaction solution (0.4 M phosphate buffer, pH 7.0) containing α-mannan (final concentration: 0.1%) and the enzyme solution, at 37° C. for 10 minutes, after which the reducing sugar was determined by the Nelson-Somogyi method with mannose as standard (Sakuzo Fukui, Seibutukagaku-jikken-hou Series 1, "Kangentou no teiryouhou (Reducing sugar quantitation methods)" (Gakkai shuppan Center), p.10 (1979)).

The α-mannosidase activities of the crude enzyme and partially purified enzyme at each purification stage were assayed by a reaction using 4-methylumbelliferyl(MU)-α-mannopyranoside as the substrate, and measurement of the free 4-MU. Specifically, the reaction was conducted in 70 µl of a reaction solution (0.15 M NaCl in 20 mM phosphate buffer, pH 7.5) containing 0.5 mM 4-MU-α-mannopyranoside and the enzyme solution, at 37° C. for 30 minutes. Subsequently, 700 µl of 0.2 M glycine buffer (pH 10.7) is added the mixture to stop the reaction. 100 µl aliquot thereof was sampled for measurement of fluorescence of free 4-MU with a microplate reader (Ex: 385 nm, Em: 450 nm). For the enzyme activity, the amount of enzyme which freed 1 mmole of 4-MU per 1 minute in this reaction, was defined as one Unit (hereinafter, "U").

The copresent contaminating enzymes was assayed as follows.

The endo-α-mannosidase activity was assayed by a reaction using α-1,6-mannan as the substrate, and subsequent measurement of the reducing ability of the free sugar. Specifically, the reaction was conducted in a reaction solution (0.4 M phosphate buffer, pH 7.0) containing α-1,6-mannan (final concentration: 0.1%) and the enzyme solution, at 37° C. for 10 minutes, after which the reducing sugar was determined by the Nelson-Somogyi method with mannose as standard (Sakuzo Fukui, Seibutukagaku-jikkenhou Series 1, "Kangentou no teiryouhou (Reducing sugar quantitation methods)" (Gakkai shuppan Center), p.10 (1979)).

The β-mannosidase activity was assayed by a reaction using p-nitrophenyl(pNP)-β-D-mannopyranoside as the substrate, and subsequent measurement of the free pNP. Specifically, the reaction was conducted in 70 μl of a reaction solution (0.15 M NaCl in 20 mM phosphate buffer, pH 7.5) containing 5 mM pNP-β-D-mannopyranoside and the enzyme solution, at 37° C. for 24 hours. Subsequently, 700 μl of 0.2 M glycine buffer (pH 10.7) is added to the mixture to stop the reaction. 100 μl aliquot thereof was sampled for measurement of the fluorescence of free 4-MU with a microplate reader (Ex: 385 nm, Em: 450 nm). For the enzyme activity, the amount of enzyme which freed 1 μmole of 4-MU per 1 minute in this reaction, was defined as one Unit (hereinafter, "U")

REFERENCE EXAMPLE 2

Screening of α-Mannosidase-Producing Cells

Medium for inducing production of mannosidase (mannan liquid medium) was prepared in the following manner. To a mixture of 2 g of baker's yeast mannan, 500 mg of ammonium sulfate [($NH_4$)$_2SO_4$], 20 mg of iron (II) sulfate [$Fe_2SO_4$], 400 mg of magnesium sulfate [$MgSO_4.7H_2O$], 60 mg of calcium chloride [$CaCl_2.2H_2O$], 1 g of yeast extract, 7.54 g of potassium diphosphate [$K_2HPO_4$] and 2.32 g of potassium monophosphate [$KH_2PO_4$] there was added water to a volume of 1 L. The flat plate medium used for isolation of the mannosidase-producing cells was prepared by adding agar powder at 1.5% to the aforementioned mannan liquid medium.

The cells in a soil suspension were inoculated to a test tube containing 2 ml of mannan liquid medium using an inoculating loop and shake cultured at 30° C. for 2 nights. The culture was again inoculated into 2 ml of fresh mannan liquid medium using an inoculating loop and further shake cultured at 30° C. for 2 nights. After a total of three cycles of the two-night shake-culturing, shake-culturing overnight was conducted twice. The culture was centrifuged and the supernatant was dialyzed against 10 mM potassium phosphate buffer (pH 7.0) to obtain a crude enzyme solution and then the crude enzyme solution was assayed for the mannan-degrading enzyme activity. Soil samples that had exhibited the activity were further screened for α-mannosidase-producing strains.

The active cultures were inoculated to a flat plate by the drawing method and dilution method, and cultured at 30° C. After several days, the appearing colonies were picked up, inoculated to mannan liquid medium and shake cultured at 30° C. for two nights. The culture was centrifuged and the supernatant was dialyzed against 10 mM potassium phosphate buffer (pH 7.0) to obtain a crude enzyme solution, and then the crude enzyme solution was assayed for the enzyme activity using α-mannan and a synthetic substrate.

After repeating this procedure several cycles, the clear single colonies were picked up to isolate a perfect α-mannosidase-producing strain. The resulting producing strain was designated as SO-5. The SO-5 was deposited internationally under FERM BP-7628 on Jun. 12, 2001 with the International Patent Organism Depositary, National Institute of Advanced Industrial Science and Technology (Tsukuba Central 6, 1-1, Higashi 1-chome, Tsukuba-shi, Tsukuba, Ibaraki, Japan).

REFERENCE EXAMPLE 3

Identification of Novel α-Mannosidase-Producing Strain SO-5

Nucleotide sequence homology of ribosomal RNA genes is important in molecular phylogeny and taxonomy. The configuration and number of copies of the ribosomal RNA genes vary depending on organism species. This allows one to identify a bacteria based on the nucleotide sequence of ribosomal RNA.

Genomic DNA was isolated from the strain SO-5 using a Wizard Genomic DNA Purification Kit (Promega). This was used as template DNA for PCR amplification of the nucleotide sequence coding for the ribosomal RNA region. The primers used were SPF1 (AGAGTTTGATCCTGGCTCAG: SEQ ID No: 5) and SPR1 (GGTTACCTTGTTACGACTT: SEQ ID No: 6). The resulting approximately 1.5 kb fragment was cloned into a PGEM-T vector (Promega), and then the nucleotide sequence was partially determined by the dideoxy method. The result is shown in SEQ ID No: 7.

A homology search was conducted for this sequence using the BLAST system, available on the Japanese DNA Databank website. As a result, it was inditated that it has high homology for both *Oerskovia xanthineolytica* and *Cellulomonas*. It was known that Oerskovia forms branching colonies, whereas SO-5 forms ordinary round colonies. This suggested that strain SO-5 was a *Cellulomonas* species.

REFERENCE EXAMPLE 4

Production and Partial Purification of α-Mannosidase

In order to induce production of α-mannosidase, strain SO-5 obtained in Reference Example 2 was cultured overnight at 30° C. in mannan liquid medium. After culturing, centrifugation was performed at 4° C., 15,000×g for 10 minutes to remove the cells. The supernatant was dialyzed against 2 mM calcium chloride in 10 mM HEPES-Na buffer (pH 7.0) to obtain a crude enzyme solution.

Next, ammonium sulfate was added to the crude enzyme solution to a final concentration of 1.2 M, and mixed overnight at 4° C. After centrifugation, the supernatant was separated from the precipitate, and ammonium sulfate was then added to a final concentration of 1.7 M prior to further mixing overnight at 4° C. The mixture was centrifuged for at 4° C., 15,000×g for 10 minutes, and the precipitating protein was collected. The obtained precipitate was dissolved in $H_2O$ and dialyzed against 2 mM calcium chloride in 10 mM HEPES-Na buffer (pH 7.0). It was then applied to a HiTrap Q column equilibrated with 2 mM calcium chloride in 10 mM HEPES-Na buffer (pH 7.0). Gradient elution was performed with increasing NaCl concentrations up to 1 M, and thus the active fraction was obtained. This was dialyzed against 2 mM calcium chloride in 10 mM HEPES-Na buffer (pH 7.0) to obtain a partially purified sample.

The partially purified preparation was assayed for α-mannosidase activity, endo-α-mannosidase activity and β-mannosidase activity according to the procedures of Reference Example 1. The specific activity was 31.9 mU/mg, and no endo-α-mannosidase activity or β-mannosidase activity was detected.

REFERENCE EXAMPLE 5

Enzymological Properties of Cellulomonas-Derived α-Mannosidase

The following examinations were performed for the purified enzyme obtained in Reference Example 4.

(a) Optimum pH: The enzyme was tested by enzyme reaction at 37° C. for 30 minutes, using sodium acetate buffers (pH 4.0-6.5), phosphate buffers (pH 6.0-8.0) and Tris buffers (pH 7.5-10.0) respectively. The optimum pH was determined to be pH 7-8, and particularly near 7.5.

(b) Optimum temperature: The enzyme was tested by reaction for 30 minutes in phosphate buffer (pH 7.5) at different temperatures of 20-80° C. The optimum temperature was determined to be 35-45° C., and particularly near 40° C.

(c) Stabilizing temperature: The enzyme was treated in 0.1 M phosphate buffer (pH 7.5) in a range of 0-80° C. for 30 minutes, and then the residual activity (relative activity) was examined by enzyme reaction at 37° C. for 30 minutes. The enzyme was stable up to 40° C.

(d) Metal ion effects: The effects of inorganic ions and inhibitors on the enzyme were examined by enzyme reaction at 37° C. for 30 minutes after adding them to a reaction system. Slight activation (10%) was produced by addition of $Ca^{2+}$. Activity was inhibited 100% by addition of $Hg^{2+}$ and ethylenediamine tetraacetate (EDTA) but activity was recovered by addition of $Ca^{2+}$.

(e) Michaelis constant: The Michaelis constant (Km) of the enzyme for 4-MU-α-mannopyranoside was determined by plotting the reciprocal substrate concentration and the reciprocal reaction rate. The Km was $0.32\ mM^{-1}$. Substrate inhibition was observed with a high concentration of substrate ($\geq 1$ mM).

(f) Action on high-mannose sugar chains: Fluorescent-labeled (PA) oligosaccharides can be separated based on their chain lengths by HPLC using an amino column. The column used was a SHODEX AsahiPak NH2P-50 (4.6×250 mm, Showa Denko). The 30:70 mixture of 200 mM acetic acid-triethylamine buffer (pH 7.0) and acetonitrile as solvent A and a 50:50 mixture of 200 mM acetic acid-triethylamine buffer (pH 7.0) and acetonitrile as solvent B were prepared as the solvents. The column was equilibrated beforehand by flowing through solvent A at a flow rate of 1.0 ml/min, and immediately after injection of the sample, the linear increasing proportion of solvent B up to 100% was applied over a period of 50 minutes, to elute the PA-oligosaccharides. The PA-oligosaccharides were detected with a fluorescent detector (excitation wavelength: 320 nm, fluorescent wavelength: 400 nm). 20 μU of the enzyme fraction of the invention was added to 100 pmol of sugar chains in 0.1 M potassium phosphate buffer (pH 7.0), at 37° C. for a period from 10 minutes to 2 hours. When Man8GlcNAc2-PA (M8) of the following structural formula:

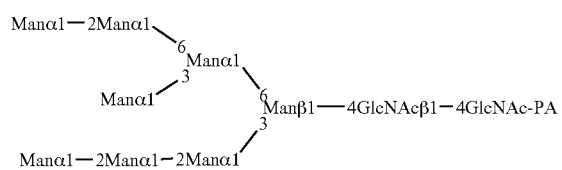

was used as the substrate, it was degraded relatively rapidly to Man5GlcNAc2-PA (M5), after which Man4GlcNAc2-PA (M4) was slowly produced, along with a small amount of Man2GlcNAc2-PA (M2). After reaction for 2 hours, 3 peaks for Man3GlcNAc2-PA (M3), Man2GlcNAc2-PA (M2) and Man1GlcNAc2-PA (M1) were also observed in addition to Man4GlcNAc2-PA. This indicated that the enzyme acts non-specifically on α-mannoside linkages, including α-1,2-mannoside linkages, α-1,3-mannoside linkage and α-1,6-mannoside linkages, at a non-reducing end. It was also predicted, based on these results, that no endo-β-N-acetylglucosaminidase would be co-present.

(g) Action on sugar chains with β-mannoside linkages: No activity was observed using p-nitrophenyl-β-D-mannoside as the substrate, thus indicating that the enzyme does not act on β-mannoside.

(h) Action on yeast phosphate-containing acidic sugar chains: It is known that an example of sugar chains produced by yeast is mannose phosphate-containing sugar chains (Kukuruzinska et al, Ann. Rev. Biochem., 56, 915-944 (1987)). The action on sugar chains having the structure shown in the following structural formula was examined.

Structural formula 7

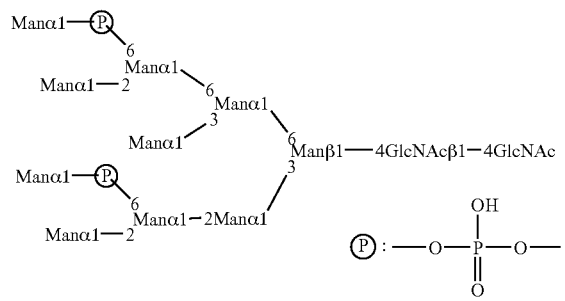

The analysis was conducted using a SuperQ 5PW (Toso). 2 mM sodium acetate buffer (pH 5.0) as solvent A and 0.25 M sodium acetate buffer (pH 5.0) as solvent B were prepared as the solvents. The column was equilibrated beforehand by flowing through solvent A at a flow rate of 1.0 ml/min, and immediately after injection of the sample, the linear increasing proportion of solvent B up to 100% was applied over a period of 30 minutes to elute the PA-oligosaccharides. 20 μU of the enzyme fraction was added to 100 pmol of sugar chains in 0.1 M potassium phosphate buffer (pH 7.0), overnight at 37° C. Sugar chains from which the phosphate-linked mannoses have been excised, elute with a delayed retention time, due to the increased negative charge of the phosphate groups. The sugar chains of the control (without enzyme) eluted near 10 minutes, while those exposed to the enzyme exhibited a additional peak after 12 minutes. Since the elution point matched the elution point of sugar chains in which the phosphate-linked mannoses had been removed from the sugar chains of Structural Formula 6 by chemical treatment. It was thus demonstrated that the enzyme is capable of cleaving phosphodiester-elinked α-mannose.

REFERENCE EXAMPLE 6

Action on Glycoprotein

Ribonuclease B (RNase B) is known as a glycoprotein with high-mannose type sugar chains. 100 μU of the α-mannosidase fraction obtained in Reference Example 2 was added to 20 μg of ribonuclease B, and the reaction was conducted at 37° C. for 14 hours in the presence of 0.1 M potassium phosphate buffer (pH 7.0). As a control, an equivalent amount of the buffer alone was added instead of the α-mannosidase fraction. Upon analysis of each by SDS-PAGE, the α-mannosidase fraction-added sample had a reduced apparent molecular weight compared to the control. The molecular weight approximated that of ribonuclease A (RNase A) having the same peptide sequence and lacking only the sugar chains. Upon assaying the ribonuclease activities, virtually no reduction in activity was found compared to before the reaction. This suggested that the enzyme fraction-added sample cleaved only the α-mannoside linkage moieties of the high-mannose type sugar chains while leaving the Manβ1-4GlcNAcβ1-4GlcNAc root moieties of the sugar chains, with no effect on the protein moieties.

EXAMPLE 4

Digestion Experiment with Different α-Mannosidases

The α-galactosidase obtained in Example 3 was treated with different α-mannosidases to determine whether the α-mannosidases act on the glycoprotein and can degrade the mannose-1-phosphate linkages of the sugar chains.

After adding 2 mU of Jack Bean α-mannosidase (Seikagaku Corp.) in sodium acetate buffer (pH 4.5) to 1 mg of the α-galactosidase purified in Example 3, the reaction was conducted overnight at 37° C. Western blot analysis for the α-galactosidase showed the same mobility as untreated α-mannosidase. The results of structural analysis of the sugar chains indicated that the mannose-1-phosphate linkages in the sugar chains had not been cleaved. It was thus concluded that mannose-1-phosphate linkages are not cleaved under these conditions.

It was therefore considered necessary to screen for a new mannosidase. Cleavage of mannose-1-phosphate linkages was attempted using the α-mannosidase from *Cellulomonas* SO-5 as described above.

Figure 8:
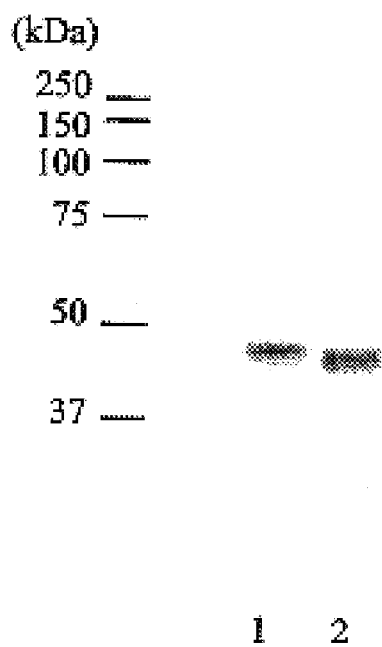
FIG. 8 is a photograph of Western blot analysis for the purified α-galactosidase which has been further treated with Cellulomonas SO-5 strain-produced α-mannosidase.
1) untreated with α-Mannosidase
2) treated with α-Mannosidase
Figure 9:
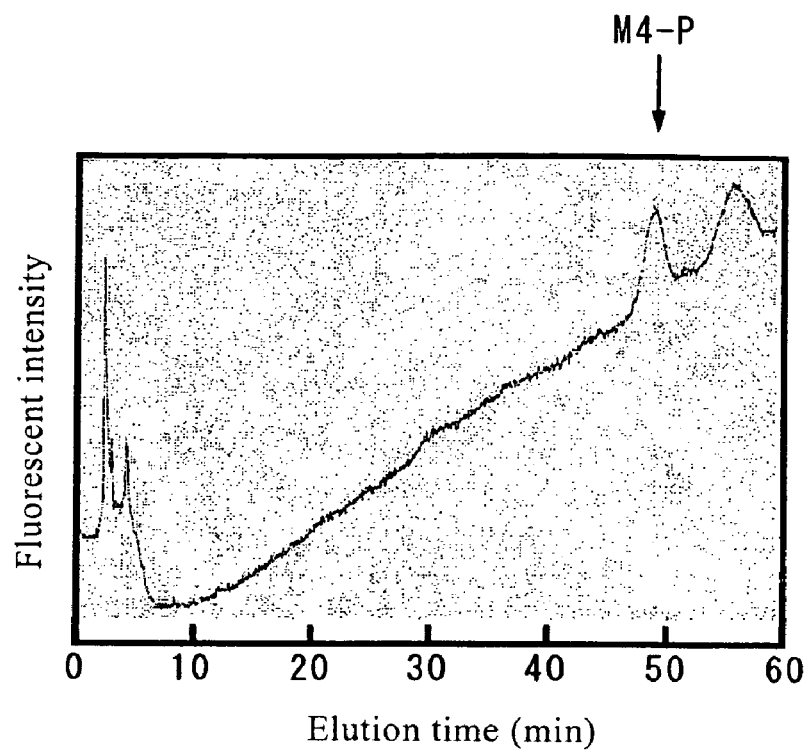
FIG. 9 shows the results of structural analysis of sugar chains obtained from α-galactosidase treated with Cellulomonas SO-5 strain-produced α-mannosidase, using an Asahi-Pak NH2-P column.

After adding 90 μU of the above-mentioned Cellulomonas SO-5-derived α-mannosidase in physiological saline buffer (PBS; pH 7.5) to 1 mg of the α-galactosidase purified in Example 3, the reaction was conducted overnight at 37° C. Western blot analysis of the α-galactosidase showed greater mobility than untreated α-mannosidase (FIG. 8). The results of structural analysis of the sugar chains of the α-galactosidase performed in the same manner as Example 3 indicated that the mannose-1-phosphate linkages of the sugar chains had been cleaved, and the elution point was the same as with exposed phosphate groups (FIG. 9).

Moreover, since elution after further alkaline phosphatase treatment occurred at the same point as Man6GlcNAc2-PA, the sugar chains obtained by treatment with α-mannosidase were demonstrated to have the structures of (PO4)2Man6GlcNAc2-PA or PO$_4$-Man4GlcNAc2-PA.

EXAMPLE 5

Large-Scale Preparation of Highly Phosphorylated Sugar Chains-Containig α-Galactosidase A large amount of α-Galactosidase having highly phosphorylated sugar chains was prepared. 30 mU of the above-mentioned *Cellulomonas* SO-5-derived α-mannosidase in Phosphate buffer (pH 7.5) was added to 300 μg of the α-galactosidase purified in Example 3 and the reaction was conducted at 37° C. for 6 hours, after which 30 mU of α-mannosidase was added and reaction was continued for 12 hours. After the reaction, purification was carried out using a MonoQ column. α-Galactosidase activity was collected in fractions 15-18 and α-mannosidase activity was collected in fractions 26-29.

EXAMPLE 6

Figure 10:
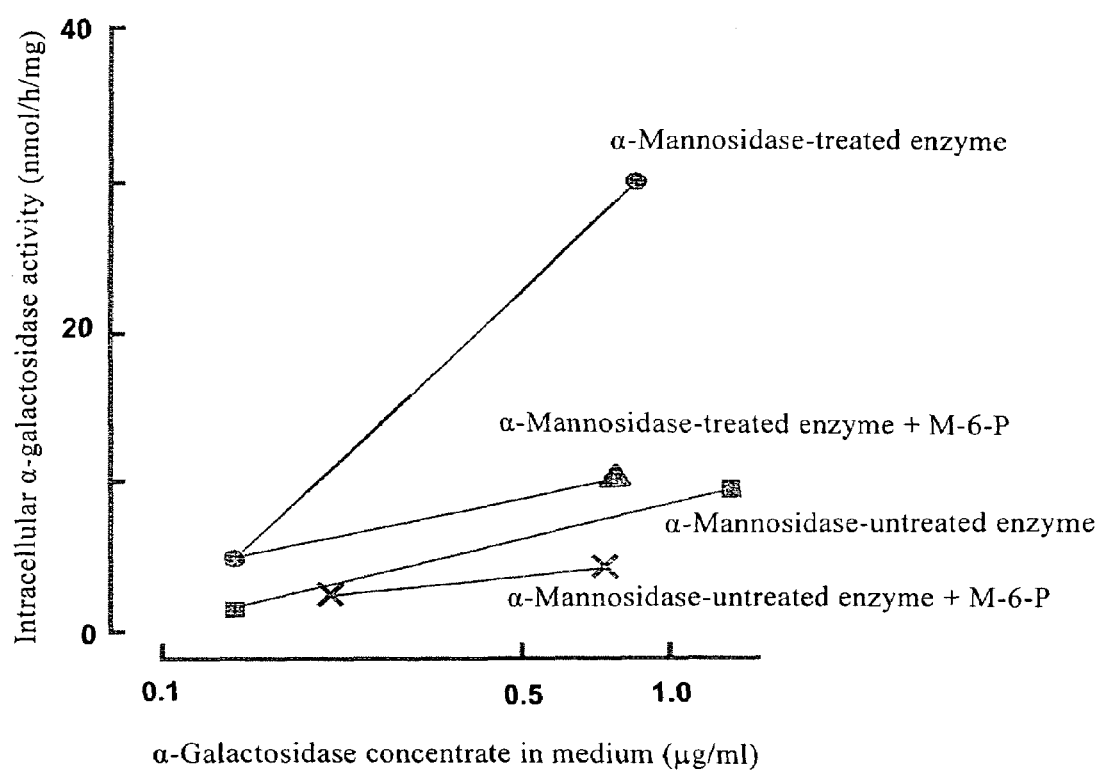
FIG. 10 shows the results of an uptake experiment (enzyme activity assay) of purified α-galactosidase obtained according to the invention, using cultured skin fibroblasts derived from a Fabry disease patient.

Uptake Experiment for Purified α-Galactosidase Using Cultured Skin Fibroblasts Obtained from Fabry Disease Patient Cultured skin fibroblasts (F377, F87) from a Fabry disease patient were cultured in Ham's F10 medium supplemented with 10% FCS in a 3.5 cm-diameter dish at 37° C. under 5% $CO_2$. Next, either mannosidase-treated α-galactosidase as in Example 5 or untreated α-galactosidase was added to the culture to a final concentration of 0.1 μg/ml or 1 μg/ml, and after 18 hours, the cells were collected and the α-galactosidase activity in the cell extract was assayed. As a control, the intracellular activity of cultured skin fibroblast cells (F592) from a normal individual was also assayed. In order to confirm mannose-6-phosphate receptor-dependent uptake, mannose-6-phosphate was added to the culture to a final concentration of 5 mM for an inhibition experiment. The results are shown in FIG. 10.

When α-galactosidase was added to a final concentration of 1 μg/ml, the α-galactosidase activity in the Fabry patient-derived cells increased approximately 3-fold using the treated enzyme with respect to the mannosidase-untreated enzyme. Also, since the increase in enzyme activity was inhibited by mannose-6-phosphate, the mannosidase-treated α-galactosidase was clearly taken up into the cells in a mannose-6-phosphate receptor-dependent manner. This suggested that the mannosidase-treated α-galactosidase had the same sugar chain structure having mannose-6-phosphate as the human enzyme.

Next, $5 \times 10^3$ cultured skin fibroblast cells (F377) from a Fabry disease patient were seeded per chamber on an 8-chamber slide by Nunc, and after culturing for 24 hours, α-galactosidase was added to 1 μg/ml. As a control, the same procedure was carried out with cultured skin fibroblast cells (F592) from a healthy human. After 18 hours or 5 days of culturing, immunofluorescent staining was carried out using antibody for the accumulated globotriosylceramide (CTH) as the primary antibody (FIG. 11).

Figure 11:
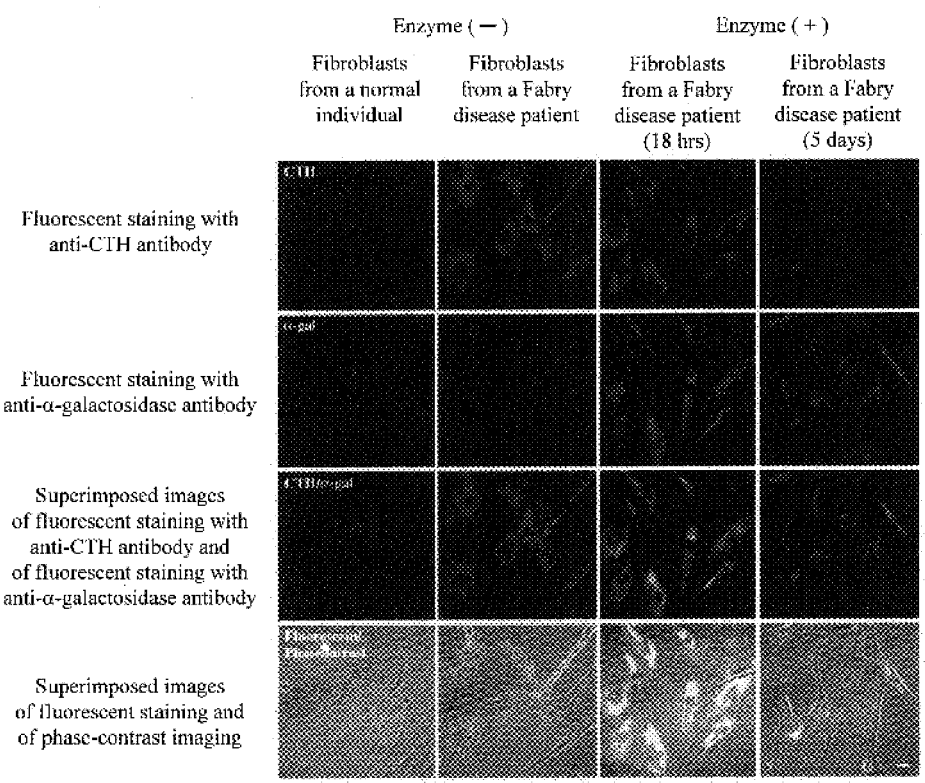
FIG. 11 is a photograph showing the effects on substrate accumulation by administration of purified α-galactosidase obtained according to the invention to cultured fibroblasts obtained from a Fabry disease patient.

The effect on accumulation of CTH in Fabry disease patient-derived cultured skin fibroblasts by adding α-galactosidase to the culture was examined by immunostaining (right of FIG. 11: enzyme (+)). The CTH was detected by treatment with anti-CTH antibody as the primary antibody followed by staining with FITC-anti-mouse IgG antibody as the secondary antibody, with visualization in green. The intracellular α-galactosidase was detected by treatment with anti-α-galactosidase antibody as the primary antibody and Cy3-anti-rabbit IgG antibody as the secondary antibody, with visualization in red. Areas where both were merged are represented in yellow. For comparison, staining of cultured skin fibroblast cells from a healthy human and α-galactosidase untreated cultured skin fibroblasts from Fabry disease patient is shown at the left (enzyme (−)).

As a result, staining with anti-CTH antibody after 5 days was clearly reduced by addition of the mannosidase-treated α-galactosidase. Moreover, since the α-galactosidase was taken up into the cells by 18 hours after addition and staining persisted even after 5 days, it was concluded to be highly stable. The fact that the accumulated CTH was degraded suggested that the α-galactosidase produced according to the invention is effective as a treatment agent for lysosomal disease.

INDUSTRIAL APPLICABILITY

The process by genetic engineering using yeast according to the present invention allows large-amount and high-purity production of a glycoprotein having a phosphate-containing acidic sugar chain in which the sugar chain can serve as a labeling marker for transporting into the lysosomes in cells of mammals such as human. The glycoprotein having a phosphate-containing acidic sugar chain according to the invention may be utilized as a drug effective, for example, in treatment of human lysosomal enzyme deficiencies.

All of the publications, patents and patent applications cited in the present specification are incorporated herein by reference, in their entirety.

The invention claimed is:

1. A process for producing an active form of a glycoprotein comprising an acidic sugar chain having a mannose-6-phosphate at a non-reducing end, comprising
  (i) expressing a gene introduced into yeast encoding said glycoprotein; and
  (ii) treating said glycoprotein with α-mannosidase obtained from *Cellulomonas* SO-5 strain bacteria (FERM BP-7628) to remove a mannose residue from the mannose-1-phosphate in the sugar chain of the glycoprotein,
wherein a-1,6-mannosyltransferase gene and a-1,3-mannosyltransferase gene have been disrupted in said yeast.

2. The process of claim 1, wherein said acidic sugar chain binds to mannose-6-phosphate receptor.

3. The process of claim 1, wherein said acidic sugar chain is a high mannose-type sugar chain consisting of the structure of one of structural formulas I to VII:

Structural formula I

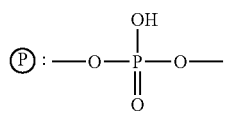

Structural formula II

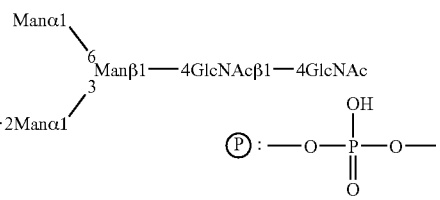

Structural formula III

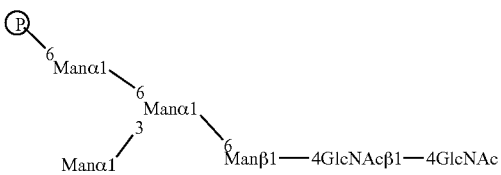

Structural formula IV

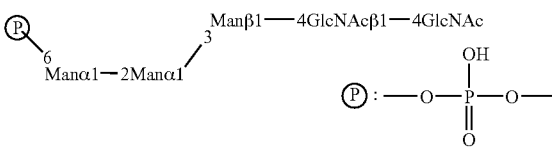

Structural formula V

Manβ1—4GlcNAcβ1—4GlcNAc

Structural formula VI

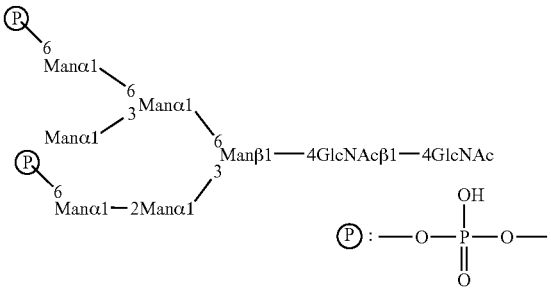

-continued

Structural formula VII

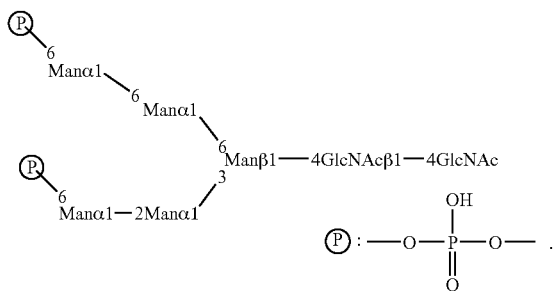

4. The process of claim 1, wherein the α-1,6-mannosyltransferase gene is the OCH1 gene of S. cerevisiae and the α-1,3-mannosyltransferase gene is the MNN1 gene of S. cerevisiae.

5. The process of claim 1, wherein the mutant yeast has a highly phosphorylated sugar chain.

6. The process of claim 1, wherein the active form of a glycoprotein having an acidic sugar chain having a mannose-6-phosphate is a lysosomal enzyme.

7. The process of claim 6, wherein the lysosomal enzyme is α-galactosidase.

8. The process of claim 7, wherein the α-galactosidase is human α-galactosidase.

9. The process of claim 8, wherein the gene encoding the α-galactosidase comprises the nucleotide sequence of SEQ ID. No: 5.

10. The process of claim 1, wherein the c~-mannosidase has an activity which non-specifically degrades α-1,2-mannoside linkages, α-1,3-mannoside linkages and α-1,6-mannoside linkages.

11. The process of claim 1, wherein the c~-mannosidase has an exo activity, and comprises no endo activity.

* * * * *

UNITED STATES PATENT AND TRADEMARK OFFICE
CERTIFICATE OF CORRECTION

PATENT NO.      : 7,579,166 B2
APPLICATION NO. : 10/480790
DATED           : August 25, 2009
INVENTOR(S)     : Chiba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1462 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer A
      for amplifying 3' region of MNN1 gene

<400> SEQUENCE: 1
ggatccgaag aaaacctaat acattgaagt                                            30

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Primer B
      for amplifying 3' region of MNN1 gene

<400> SEQUENCE: 2
gcatgccctt tggtttaata taaatctccg gagtgc                                     36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer C
      for amplifying 5' region of MNN1 gene

<400> SEQUENCE: 3
gcatgctaca taactccaat cagcagcaaa tatgtc                                     36

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Primer D
      for amplifying 5' region of MNN1 gene

<400> SEQUENCE: 4
gcggccgcgt gttctgttcg ggtaacgttt aaaccaat                                   38

<210> SEQ ID NO 5
<211> LENGTH: 1306
<212> TYPE: DNA
<213> ORGANISM: Homo sapiens
<220> FEATURE:
<221> NAME/KEY: CDS
<222> LOCATION: (17)(1306)

<400> SEQUENCE: 5
```

```
tccggtcacc gtgacaatgc agctgaggaa cccagaacta catctgggct gcgcgcttgc      60
gcttcgcttc ctggccctcg tttcctggga catccctggg gctagagcac tggacaatgg     120
attggcaagg acgcctacca tgggctggct gcactgggag cgcttcatgt gcaaccttga     180
ctgccaggaa gagccagatt cctgcatcag tgagaagctc ttcatggaga tggcagagct     240
catggtctca gaaggctgga aggatgcagg ttatgagtac ctctgcattg atgactgttg     300
gatggctccc caaagagatt cagaaggcag acttcaggca gaccctcagc gctttcctca     360
tgggattcgc cagctagcta attatgttca cagcaaagga ctgaagctag ggatttatgc     420
agatgttgga aataaaacct gcgcaggctt ccctgggagt tttggatact acgacattga     480
tgcccagacc tttgctgact ggggagtaga tctgctaaaa tttgatggtt gttactgtga     540
cagtttggaa aatttggcag atggttataa gcacatgtcc ttggccctga ataggactgg     600
cagaagcatt gtgtactcct gtgagtggcc tctttatatg tggccctttc aaaagcccaa     660
ttatacagaa atccgacagt actgcaatca ctggcgaaat tttgctgaca ttgatgattc     720
ctggaaaagt ataaagagta tcttggactg acatcttttt aaccaggaga gaattgttga     780
tgttgctgga ccaggggggtt ggaatgaccc agatatgtta gtgattggca actttggcct     840
cagctggaat cagcaagtaa ctcagatggc cctctgggct atcatggctg ctcctttatt     900
catgtctaat gacctccgac acatcagccc tcaagccaaa gctctccttc aggataagga     960
cgtaattgcc atcaatcagg acccccttggg caagcaaggg taccagctta gacagggaga    1020
caactttgaa gtgtgggaac gacctctctc aggcttagcc tgggctgtag ctatgataaa    1080
ccggcaggag attggtggac ctcgctctta taccatcgca gttgcttccc tgggtaaagg    1140
agtggcctgt aatcctgcct gcttcatcac acagctcctc cctgtgaaaa ggaagctagg    1200
gttctatgaa tggacttcaa ggttaagaag tcacataaat cccacaggca ctgttttgct    1260
tcagctagaa aatacaatgc agatgtcatt aaaagactta ctttaa                   1306

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer SPF1

<400> SEQUENCE: 6
agagtttgat cctggctcag                                                  20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer SPR1

<400> SEQUENCE: 7
ggttaccttg ttacgactt                                                   19

<210> SEQ ID NO 8
<211> LENGTH: 619
<212> TYPE: DNA
<213> ORGANISM: Cellulomonas sp.

<400> SEQUENCE: 8
ggatgaaggc cttcgggttg taaacctctt tcagcaggga agaagcgcaa gtgacggtac      60
ctgcagaaga agcgccggct aactacgtgc cagcagccgc ggtaatacgt agggcgcaac     120
```

-continued

```
gttgtccgga attattgggc gtaaagagct cgtaggcggt ttgtcgcgtc tggtgtgaaa    180
actcgaggct caacctcgag cttgcatcgg gtacgggcag actagagtgc ggtaggggag    240
actggaattc ctggtgtagc ggtggaatgc gcagatatca ggaggaacac cgatggcgaa    300
ggcaggtctc tgggccgcaa ctgacgctga ggagcgaaag catgggagc gaacaggatt     360 agataccctg gtagtccatg ccgtaaacgt tgggcactag gtgtggggct cattccacga    420
gttccgtgcc gcagcaaacg cattaagtgc cccgcctggg gagtacggcc gcaaggctaa    480
aactcaaagg aattgacggg ggcccgcaca agcggcggag catgcggatt aattcgatgc    540
aacgcgaaga accttaccaa ggcttgacat gcacgggaag ccaccagaga tggtggtctc    600
tttggacact cgtgcacag                                                 619
```